(12) United States Patent
Ishimaru

(10) Patent No.: US 8,830,462 B2
(45) Date of Patent: Sep. 9, 2014

(54) OPTICAL CHARACTERISTIC MEASUREMENT DEVICE AND OPTICAL CHARACTERISTIC MEASUREMENT METHOD

(75) Inventor: Ichiro Ishimaru, Takamatsu (JP)

(73) Assignee: National University Corporation Kagawa University, Takamatsu (JP)

( * ) Notice: Subject to any disclaimer, the term of this patent is extended or adjusted under 35 U.S.C. 154(b) by 0 days.

(21) Appl. No.: 14/001,810

(22) PCT Filed: Feb. 28, 2012

(86) PCT No.: PCT/JP2012/054940
§ 371 (c)(1),
(2), (4) Date: Aug. 27, 2013

(87) PCT Pub. No.: WO2012/118079
PCT Pub. Date: Sep. 7, 2012

(65) Prior Publication Data
US 2013/0335740 A1    Dec. 19, 2013

(30) Foreign Application Priority Data
Feb. 28, 2011 (JP) ................. 2011-043170

(51) Int. Cl.
*G01J 4/00* (2006.01)
*G01J 3/02* (2006.01)
*G01J 3/453* (2006.01)
*G01N 21/23* (2006.01)

(52) U.S. Cl.
CPC ............. *G01N 21/23* (2013.01); *G01J 3/0224* (2013.01); *G01J 3/453* (2013.01)
USPC ....................................................... 356/365

(58) Field of Classification Search
CPC . G01N 21/21; G01N 21/9501; G01N 21/211; G01N 21/55; G01N 21/23; G01N 21/8806; G01N 21/956; G01N 21/4738; G01N 21/41; G01N 21/552; G01N 21/553; G01N 2021/0346; G01N 2021/4792; G01N 2021/8822
See application file for complete search history.

(56) References Cited

U.S. PATENT DOCUMENTS 7,061,613 B1 * 6/2006 Huang et al. ................... 356/364
8,125,641 B2 * 2/2012 Li ................................... 356/369

FOREIGN PATENT DOCUMENTS

JP    A 2001-141602    5/2001

OTHER PUBLICATIONS

Uraki et al; "Proposal of the One-shot real-time Fourier spectroscopic imaging;" Optics & Photonics Japan; Nov. 8, 2010; pp. 84-85.

(Continued)

*Primary Examiner* — Michael P Stafira
(74) *Attorney, Agent, or Firm* — Oliff PLC

(57) ABSTRACT

A linearly polarized light reaches a sample S through a polarizer and receives a retardation from the sample S. Then, the light reaches a movable mirror unit and a fixed mirror unit of a phase shifter through a first polarizing plate and a second polarizing plate. Then, the reflected measurement lights pass through an analyzer, and are caused by an imaging lens to form an interference image on the light-receiving surface of a detector. At this time, an optical path length difference between a beam reflected on the movable mirror unit and a beam reflected on the fixed mirror unit is continuously changed the movable mirror unit. Hence, the imaging intensity of the interference image detected by the detector continuously changes producing a synthetic waveform similar to an interferogram. The synthetic waveform is Fourier-transformed, to obtain an amplitude per wavelength and a birefringent phase difference per wavelength.

15 Claims, 15 Drawing Sheets

(56) References Cited

OTHER PUBLICATIONS

Otani; Polarimetry and interferometry; Optronics; Aug. 9, 2010; No. 8; pp. 111-116.
Wakayama et al; "2D measurement of birefringence dispersion by spectroscopic polarized light;" Japan Society for Laser Microscopy Koenkai Ronbusunshu; 2002; pp. 77-81.
Kobayashi et al; "Evaluation Methods for Stone Artifact using Polarization Measurement;" Chino Mechatronics Workshop Koen Ronbunshu; Jan. 12, 2011.

Jun. 5, 2012 Search Report issued in International Patent Application No. PCT/JP2012/054940.
Jun. 5, 2012 Written Opinion issued in International Patent Application No. PCT/JP2012/054940 (with translation).
Sep. 3, 2013 International Preliminary Report on Patentability issued in International Patent Application No. PCT/JP2012/054940 (with translation).

\* cited by examiner

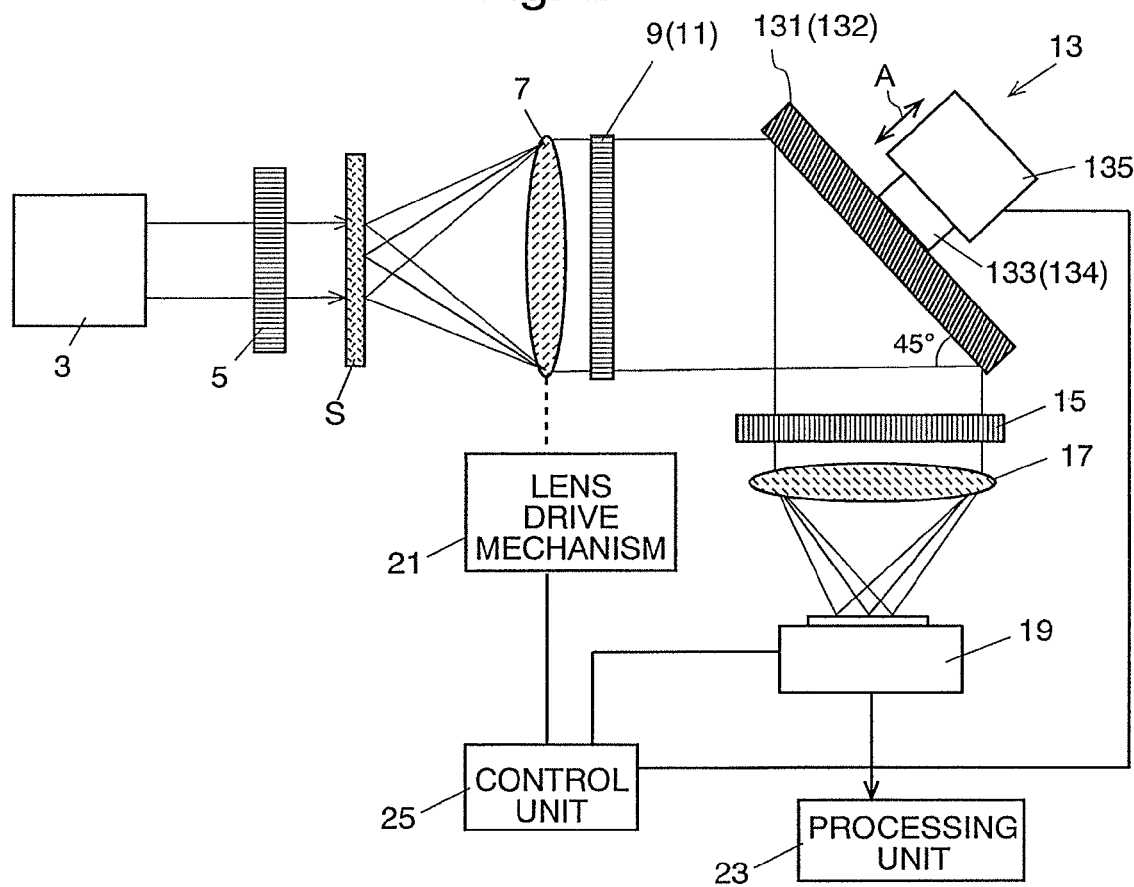

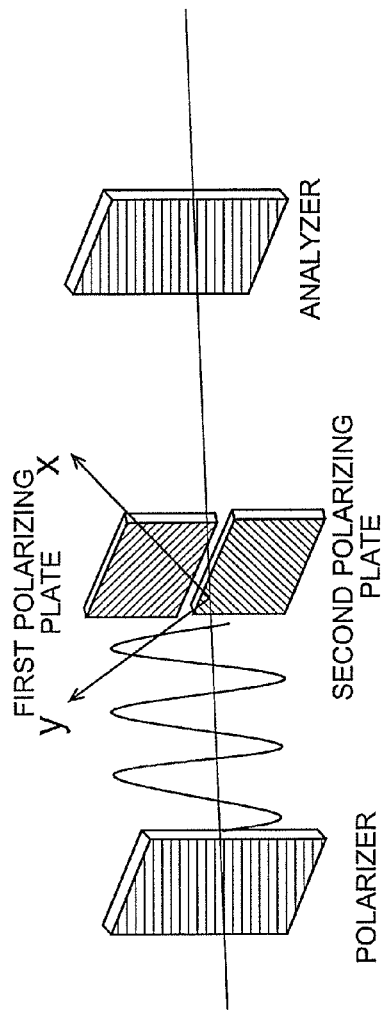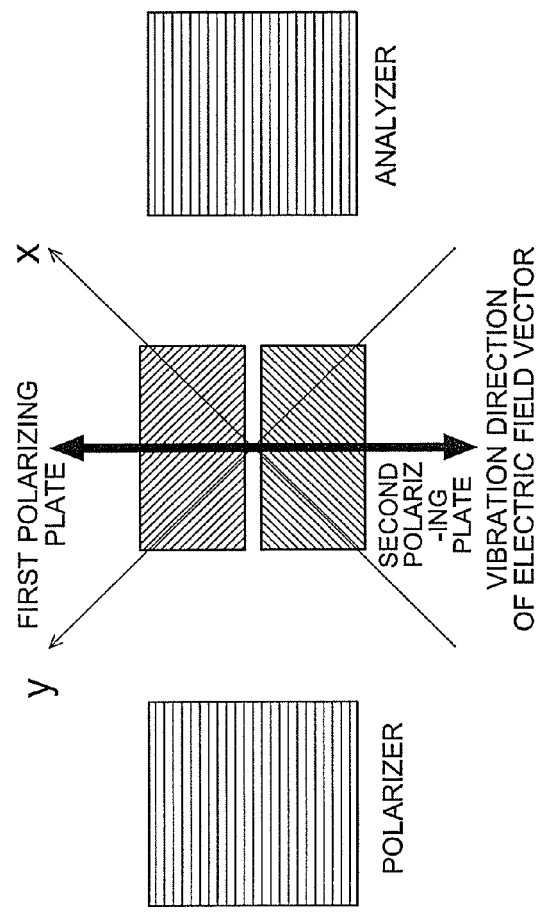

LIGHT TRAVELLING DIRECTION

RETARDATION AMOUNT

LIGHT-RECEIVING SURFACE
(IMAGING PLANE)

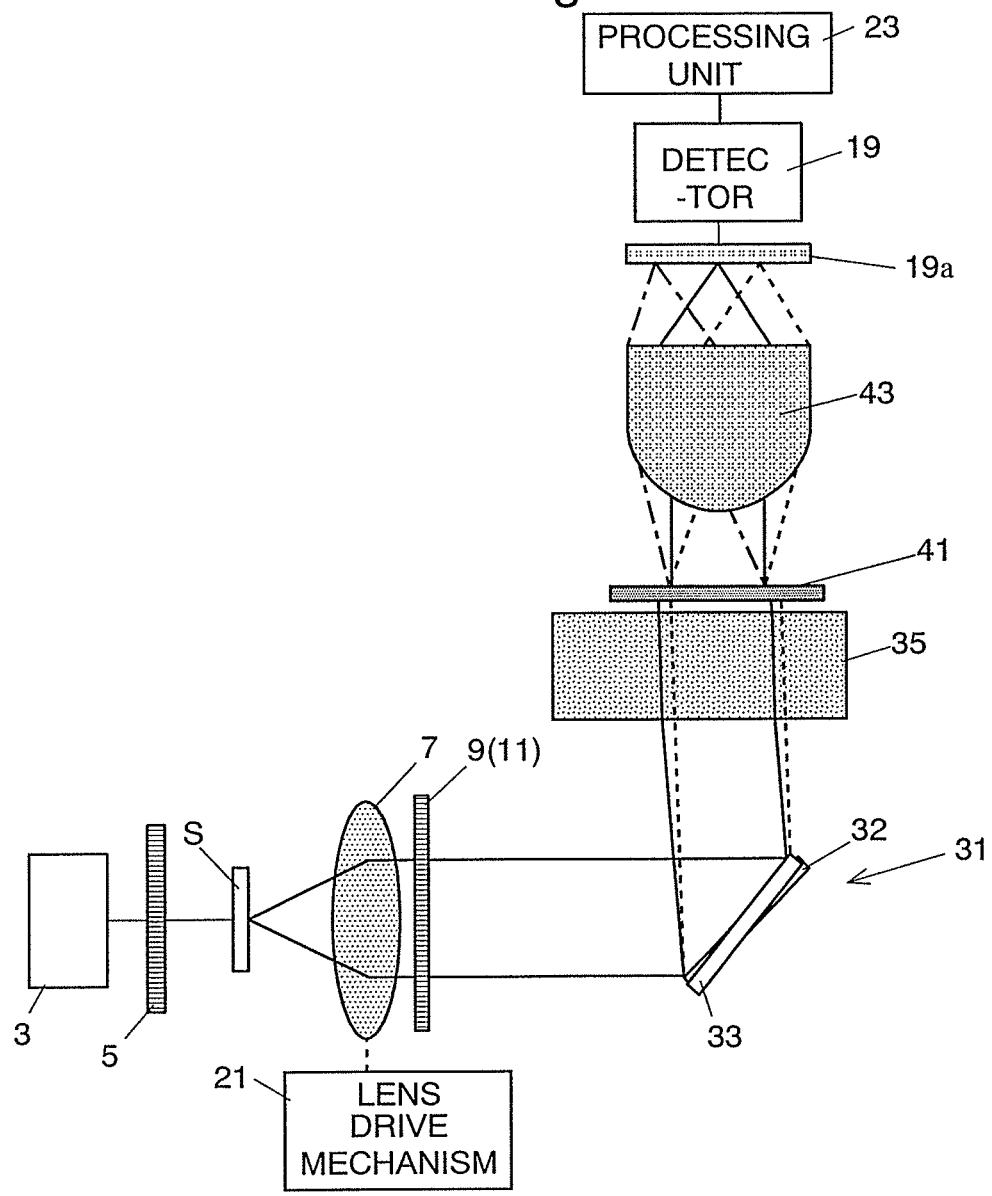

OPTICAL CHARACTERISTIC MEASUREMENT DEVICE AND OPTICAL CHARACTERISTIC MEASUREMENT METHOD

TECHNICAL FIELD

The present invention relates to an optical characteristic measurement device and an optical characteristic measurement method capable of measuring both spectral characteristics and polarization characteristics of a substance.

BACKGROUND ART

Up to now, a method of measuring optical characteristics of a substance to thereby estimate an unknown component in the substance has been known. For example, JP-A 2001-141602 discloses a method of estimating an unknown component, including obtaining a birefringent phase difference (retardation) from the transmitted light intensity when light is transmitted through a substance as a measurement target, and calculating an index of birefringence inherent in the substance from the birefringent phase difference. Birefringence refers to a phenomenon in which two refracted lights appear when light enters an anisotropic medium. A birefringent phase difference is expressed by the product of an index of birefringence and a transmitted light path length. Hence, if the transmitted light path length of the light is different even if the birefringent phase difference is the same, the index of birefringence is also different. Accordingly, an accurate index of birefringence can be obtained using a transmitted light path length accurately determined for a measured birefringent phase difference.

It is unfortunately difficult to obtain an accurate index of birefringence, in the case where the transmitted light path length cannot be easily obtained for a measurement target, for example, in the case where the shape of the measurement target is complicated. Further, in the case where the measurement target is a biological membrane such as the retina of an eye, the measurement target cannot be cut out of a human body, and hence its thickness, that is, the transmitted light path length cannot be measured.

Further, a method of estimating an unknown component in a substance from Fourier spectral characteristics, which are optical characteristics other than birefringent properties, has been known. As described above, birefringent properties are optical characteristics observed when a substance is an anisotropic medium, and hence it is effective to measure both birefringent properties and Fourier spectral characteristics in estimating components of an unknown substance. Unfortunately, conventional devices are not capable of measuring both Fourier spectral characteristics and birefringent properties at the same time.

BACKGROUND ART DOCUMENT

Patent Document

[Patent Document 1] JP-A 2001-141602

DISCLOSURE OF THE INVENTION

Problems to be Solved by the Invention

An objective of the present invention is to provide an optical characteristic measurement device and an optical characteristic measurement method capable of simultaneously measuring both Fourier spectral characteristics and birefringent properties of substances having various shapes and properties.

Means for Solving the Problems

To solve the aforementioned problem, an optical characteristic measurement device according to the present invention includes: a) a division optical system for directing a light emitted from an object to be measured, on which a linearly polarized light is incident, to a first polarizing plate and a second polarizing plate; b) an analyzer for allowing a synthetic light in a predetermined polarization direction to be transmitted therethrough, the synthetic light being made of a first polarization component transmitted through the first polarizing plate and a second polarization component transmitted through the second polarizing plate; c) an imaging optical system for directing the synthetic light transmitted through the analyzer to a single point so as to thereby form an interference image; d) a detection unit for detecting a light intensity of the interference image; e) a phase difference changer for changing a difference in optical path length between the first polarization component and the second polarization component that respectively travel from the first polarizing plate and the second polarizing plate to the analyzer, to thereby change a phase difference between the first polarization component and the second polarization component; and f) a processing unit for Fourier-transforming data of a change in light intensity detected by the detection unit along with the change in phase difference, to thereby acquire an amplitude per wavelength and a birefringent phase difference per wavelength of the light emitted from the object to be measured.

An optical characteristic measurement device according to the present invention includes: a) a division optical system for directing a light emitted from an object to be measured, on which a linearly polarized light is incident, to a first polarizing plate and a second polarizing plate; b) an analyzer for allowing a synthetic light in a predetermined polarization direction to be transmitted therethrough, the synthetic light being made of a first polarization component transmitted through the first polarizing plate and a second polarization component transmitted through the second polarizing plate; c) an imaging optical system for focusing the synthetic light transmitted through the analyzer on a single straight line that extends in a direction different from those of optical axes of the first polarization component and the second polarization component, to thereby form a linear interference image; d) a phase changer for giving a continuous optical path length difference distribution between the first polarization component and the second polarization component that respectively travel from the first polarizing plate and the second polarizing plate to the analyzer, to thereby give a continuous phase change between the first polarization component and the second polarization component; e) a detection unit for detecting a light intensity distribution of the linear interference image along a direction in which the interference image extends; and f) a processing unit for Fourier-transforming data indicating the light intensity distribution of the interference image detected by the detection unit, to thereby acquire an amplitude per wavelength and a birefringent phase difference per wavelength of the light emitted from the object to be measured.

An optical characteristic measurement device according to the present invention includes: a) a division optical system for directing a light emitted from an object to be measured, on which a linearly polarized light is incident, to a first polarizing plate and a second polarizing plate; b) an analyzer for allowing a synthetic light in a predetermined polarization direction to be transmitted therethrough, the synthetic light being made of a first polarization component transmitted through the first polarizing plate and a second polarization component transmitted through the second polarizing plate; c) an imaging optical system for focusing the synthetic light transmitted through the analyzer on a single straight line that extends in a direction different from those of optical axes of the first polarization component and the second polarization component, to thereby form a linear interference image; d) a phase changer for giving a continuous optical path length difference distribution between the first polarization component and the second polarization component that respectively travel from the first polarizing plate and the second polarizing plate to the analyzer, to thereby give a continuous phase change between the first polarization component and the second polarization component; e) a spectral optical system for wavelength-resolving the linear interference image, to thereby form an optical spectrum; f) a detection unit for detecting a light intensity distribution of the optical spectrum; and g) a processing unit for acquiring an amplitude per wavelength and a birefringent phase difference per wavelength of the light emitted from the object to be measured, from the light intensity distribution detected by the detection unit.

In any of the above-mentioned optical characteristic measurement devices according to the present invention, it is preferable that the first polarizing plate and the second polarizing plate be arranged such that polarization directions of the first polarization component and the second polarization component are orthogonal to each other, and are inclined by 45 degrees with respect to an electric field component of the linearly polarized light that enters the object to be measured.

In any of the above-mentioned optical characteristic measurement devices according to the present invention, it is preferable that the division optical system include an objective lens for collimating the light emitted from the object to be measured into parallel light rays and directing the parallel light rays to the first polarizing plate and the second polarizing plate, and that the processing unit acquire an amplitude per wavelength and a birefringent phase difference per wavelength (amount of phase difference) of a light emitted from a part of the object to be measured, the part corresponding to a focal point of the objective lens.

In this case, it is preferable that any of the above-mentioned optical characteristic measurement devices according to the present invention further include a focal point changer for relatively changing the focal point of the objective lens with respect to the object to be measured.

Further, an optical characteristic measurement method according to the present invention includes: a) causing a linearly polarized light to enter an object to be measured; b) directing, by a division optical system, a light emitted from the object to be measured, on which the linearly polarized light is incident, to a first polarizing plate and a second polarizing plate; c) directing a first polarization component transmitted through the first polarizing plate and a second polarization component transmitted through the second polarizing plate to an imaging optical system through an analyzer, while changing a difference in optical path length between the first polarization component and the second polarization component, and focusing, by the imaging optical system, the directed components on a single point, to thereby form an interference image; and d) Fourier-transforming data indicating a change in light intensity of the interference image, to thereby acquire an amplitude per wavelength and a birefringent phase difference per wavelength of the light emitted from the object to be measured.

An optical characteristic measurement method according to the present invention includes: a) causing a linearly polarized light to enter an object to be measured; b) directing, by a division optical system, a light emitted from the object to be measured, on which the linearly polarized light is incident, to a first polarizing plate and a second polarizing plate; c) directing a first polarization component transmitted through the first polarizing plate and a second polarization component transmitted through the second polarizing plate to an imaging optical system through an analyzer, while giving a continuous optical path length difference distribution between the first polarization component and the second polarization component, and focusing, by the imaging optical system, the directed components on a single straight line, to thereby form a linear interference image; and d) Fourier-transforming data indicating a light intensity distribution of the linear interference image along a direction in which the interference image extends, to thereby acquire an amplitude per wavelength and a birefringent phase difference per wavelength of the light emitted from the object to be measured.

An optical characteristic measurement method according to the present invention includes: a) causing a linearly polarized light to enter an object to be measured; b) directing, by a division optical system, a light emitted from the object to be measured, on which the linearly polarized light is incident, to a first polarizing plate and a second polarizing plate; c) directing a first polarization component transmitted through the first polarizing plate and a second polarization component transmitted through the second polarizing plate to an imaging optical system through an analyzer, while giving a continuous optical path length difference distribution between the first polarization component and the second polarization component, and focusing, by the imaging optical system, the directed components on a single straight line, to thereby form a linear interference image; d) wavelength-resolving, by a spectral optical system, the linear interference image, to thereby acquire an optical spectrum; and e) acquiring an amplitude per wavelength and a birefringent phase difference per wavelength of the light emitted from the object to be measured, based on a light intensity distribution of the optical spectrum.

Effects of the Invention

According to an optical characteristic measurement device and an optical characteristic measurement method according to the present invention, a light emitted from an object to be measured on which a linearly polarized light is incident is directed to a first polarizing plate and a second polarizing plate by a division optical system, and is transmitted through the first polarizing plate and the second polarizing plate to become a synthetic light being made of a first polarization component and a second polarization component. Then, the synthetic light enter an analyzer. The synthetic light transmitted through the analyzer is directed to a single point or a single straight line by an imaging optical system, to thereby form an interference image. At this time, a phase difference between the first polarization component and the second polarization component changes temporally or spatially, and hence the intensity of an interference light detected by a detection unit changes, so that a synthetic waveform similar to an interferogram is acquired. If the synthetic waveform is Fourier-transformed by a processing unit, an amplitude per wavelength and a birefringent phase difference per wavelength of the light emitted from the object to be measured can be obtained, and hence Fourier spectral characteristics and birefringent properties of the object to be measured can be obtained at the same time.

Note that, in the case where two lights are directed to a single "point" to interfere with each other, not an "interference image" but an "interference light" is formed in a strict sense, but what is formed by two lights that interfere with each other is all referred to as "interference image" herein.

Further, according to the present invention, whether the light emitted from the object to be measured, on which the linearly polarized light is incident is a transmitted light or a reflected light, Fourier spectral characteristics and birefringent properties of the object to be measured can be obtained at the same time using this light. Accordingly, the object to be measured can include not only products having a relatively simple configuration, such as an optical element and a polymer film, but also substances having a complicated configuration and biological membranes, such as the retina of an eye, and hence the present invention can be applied to a wide field.

In conventional Fourier transform infrared spectroscopy (FTIR), a light emitted from an object to be measured is split into two using a Michelson-type interferometer, the two split lights are directed to a common optical path so as to interfere with each other, and the resultant interference light is detected by a detector. Since the two split lights interfere with each other on the common optical path, the mixed interference light of lights emitted from various positions (depths) in the object to be measured exists on the light-receiving surface of the detector.

In contrast, according to the present invention, the light emitted from the object to be measured is divided into the first polarization component and the second polarization component by the division optical system, and these polarization components are directed to the imaging optical system through different optical paths, and are then focused on a single point by the imaging optical system so as to interfere with each other. Only lights emitted from a focal plane interfere with each other on the imaging plane of the imaging optical system. Hence, in the present invention, the light-receiving surface of the detection unit is located on the imaging plane of the imaging optical system, whereby only the interference light of lights emitted from a part of the object to be measured corresponding to the focal plane, that is, from a particular depth in the object to be measured can be detected by the detection unit. As a result, a clear interference image with small noise can be obtained.

BRIEF DESCRIPTION OF THE DRAWINGS

FIG. 2 is a view showing a schematic overall configuration of the optical characteristic measurement device.

FIGS. 3A and 3B are views for describing polarization directions of a polarizer, a first polarizing plate, a second polarizing plate, and an analyzer.

FIG. 4A shows a linear polarization component and electric field components obtained by subjecting the linear polarization component to vector decomposition into x-directional and y-directional orthogonal components, and FIG. 4B shows the linear polarization component and the x-directional and y-directional electric field components, which are taken in a light travelling direction.

FIG. 22 is a view showing a schematic overall configuration of an optical characteristic measurement device according to a fourth embodiment of the present invention.

BEST MODES FOR CARRYING OUT THE INVENTION

Hereinafter, some specific embodiments of the present invention are described with reference to the drawings.

First Embodiment

Figure 1:
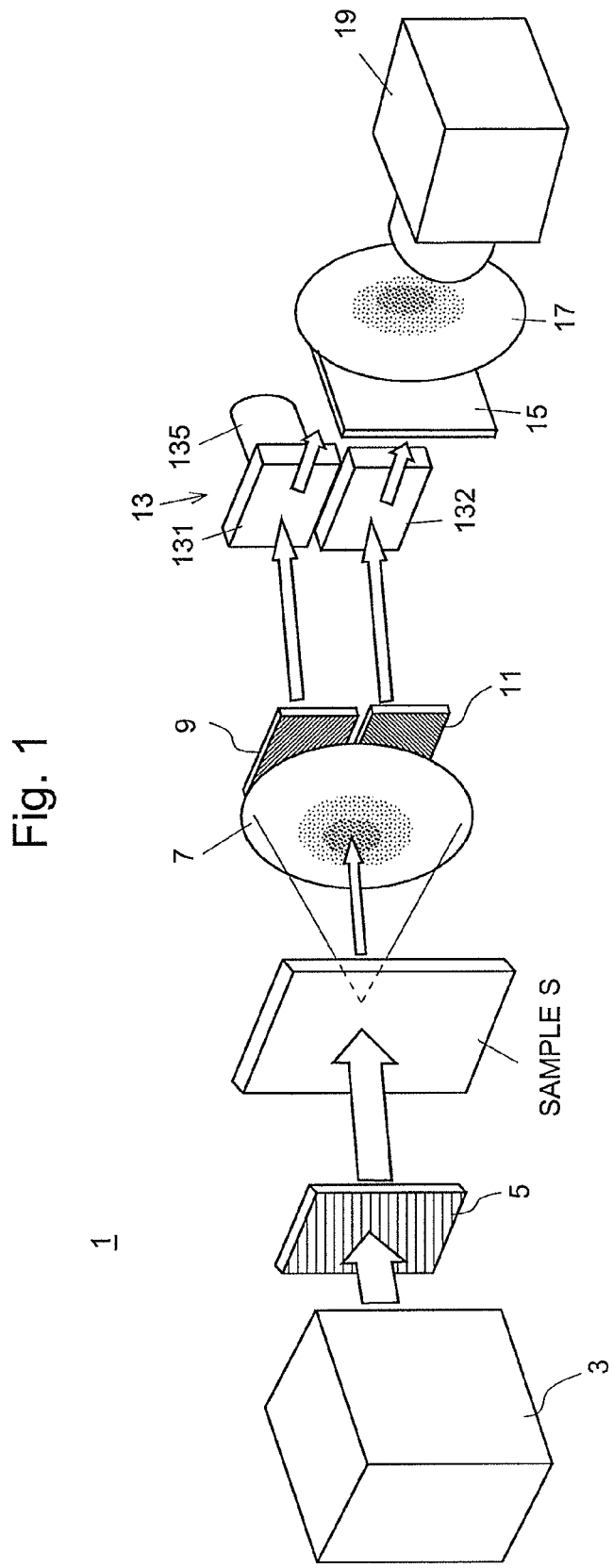
FIG. 1 is a schematic view showing an overall configuration of an optical characteristic measurement device and an arrangement of optical elements according to a first embodiment of the present invention.

FIG. 1 and FIG. 2 each show an optical characteristic measurement device according to a first embodiment. As shown in FIG. 1 and FIG. 2, an optical characteristic measurement device 1 according to the first embodiment includes a light source 3, a polarizer 5, an objective lens 7, a first polarizing plate 9, a second polarizing plate 11, a phase shifter 13, an analyzer 15, an imaging lens 17, and a detector 19. In the present embodiment, the objective lens 7, the first polarizing plate 9, and the second polarizing plate 11 form a division optical system, and the imaging lens 17 forms an imaging optical system. Further, the phase shifter 13 functions as a phase difference changer.

The objective lens 7 can be moved in the direction of its optical axis by means of a lens drive mechanism 21. The lens drive mechanism 21 is used for shifting the focal point of the objective lens 7, and corresponds to a focal point changer. The lens drive mechanism 21 may be composed of a piezo element, for example.

The polarizer 5 is arranged on the optical path of a light emitted from the light source 3, and extracts only a linear polarization component in a particular direction from the light, to deliver the extracted component onto a sample S that is an object to be measured. After the light is delivered onto the sample S, the light transmitted through the sample S (hereinafter, also referred to as "measurement light") enters the objective lens 7, and is converted into parallel beams.

Note that, although FIG. 1 and FIG. 2 each show the transmissive optical characteristic measurement device 1 for measuring the light transmitted through the sample S, a reflective optical characteristic measurement device for measuring the light that has been reflected on the inside of the sample S may be adopted. This is because both of the light transmitted through the sample and the light that has been reflected on the inside of the sample have birefringent properties and light absorption characteristics of components in the sample.

Further, after being transmitted through the objective lens 7, the beams do not have to be perfect parallel beams. As described later, the objective lens 7 just has to widen the measurement light such that the measurement light can be divided into two or more beams. However, non-parallel beams are likely to cause an error in the amount of phase difference, which depends on the phase shift amount to be described later. Accordingly, it is desirable to use parallel beams as much as possible in order to enhance the measurement accuracy.

Both of the first polarizing plate 9 and the second polarizing plate 11 are arranged, for example, one above the other on the optical path of the parallel beams that have been transmitted through the objective lens 7. The parallel beams that have been transmitted through the objective lens 7 reach the phase shifter 13 through the first polarizing plate 9 and the second polarizing plate 11.

As shown in FIGS. 3A and 3B, the first polarizing plate 9 and the second polarizing plate 11 are set such that the polarization directions thereof are each inclined by 45 degrees with respect to the vibration direction of the electric field vector of the linear polarization component transmitted through the polarizer 5 and that the polarization direction of the first polarizing plate 9 and the polarization direction of the second polarizing plate 11 are orthogonal to each other. In the following description, the polarization direction of the first polarizing plate 9 is also referred to as x direction, and the polarization direction of the second polarizing plate 11 is also referred to as y direction. Further, the light transmitted through the first polarizing plate 9 is referred to as first polarized light, and the light transmitted through the second polarizing plate 11 is referred to as second polarized light.

The phase shifter 13 includes: a rectangular plate-like movable mirror unit 131; a rectangular plate-like fixed mirror unit 132 arranged below the movable mirror unit 131; holders 133 and 134 for respectively holding the movable mirror unit 131 and the fixed mirror unit 132; and a drive stage 135 for moving the holder 133 of the movable mirror unit 131. The first polarized light transmitted through the first polarizing plate 9 enters the movable mirror unit 131, and the second polarized light transmitted through the second polarizing plate 11 enters the fixed mirror unit 132. The surfaces (reflection surfaces) of the movable mirror unit 131 and the fixed mirror unit 132 are optically flat, and are optical mirror surfaces that can reflect lights in wavelength ranges to be measured by the device 1. Further, the sizes of the reflection surfaces of the movable mirror unit 131 and the fixed mirror unit 132 are substantially the same.

Note that, in the following description, the beam that reaches the reflection surface of the movable mirror unit 131 from the first polarizing plate 9 and is reflected thereon to reach the analyzer 15 is also referred to as movable beam, and the beam that reaches the reflection surface of the fixed mirror unit 132 from the second polarizing plate 11 and is reflected thereon to reach the analyzer 15 is also referred to as fixed beam.

The drive stage 135 is composed of, for example, a piezo element including a capacitance sensor, and moves the holder 133 in an arrow A direction upon reception of a control signal from a control unit 25. Consequently, the movable mirror unit 131 moves in the arrow A direction with precision suited to each light wavelength. As a result, an optical path length difference occurs between the movable beam and the fixed beam, and a relative phase change is provided between these two beams. Accordingly, in the present embodiment, the phase shifter 13 corresponds to an optical path length difference changer, and the movable mirror unit 131 and the fixed mirror unit 132 respectively correspond to a first reflection unit and a second reflection unit. Depending on spectrometric capability, high-precision position control of approximately 10 nm is necessary, for example, in a visible light region.

Further, the phase shifter 13 is arranged such that the reflection surfaces of the movable mirror unit 131 and the fixed mirror unit 132 are each inclined by 45 degrees with respect to the optical axis of the parallel beams from the objective lens 7. The drive stage 135 moves the movable mirror unit 131 while keeping the inclination of the reflection surface of the movable mirror unit 131 with respect to the optical axis at 45 degrees. With such a configuration, the amount of movement of the movable mirror unit 131 in the optical axis direction is √2 of the amount of movement of the drive stage 135. Further, the optical path length difference for giving a relative phase change between the fixed beam and the movable beam is twice as large as the amount of movement of the movable mirror unit 131 in the optical axis direction.

This oblique positioning of the movable mirror unit 131 and the fixed mirror unit 132 can eliminate a beam splitter for dividing a light ray, and hence the use efficiency of an object light can be enhanced.

The analyzer 15 is set in a so-called open nicol state, in which a linear polarization component in the same direction as that of the polarizer 5 is transmitted therethrough. Accordingly, in the case where the sample S does not have birefringent properties, if a phase shift operation is not performed, a linear polarization component that has passed through the polarizer 5 from the light source 3 and has been transmitted through the measurement target reaches the imaging lens 17 as it is. The light-receiving surface of the detector 19 is located at a position corresponding to the imaging plane of the imaging lens 17, and the linear polarization component that has reached the imaging lens 17 is focused on a single point on the light-receiving surface of the detector 19. Note that the analyzer 15 may be set so as to have a polarization extraction angle of 45 degrees with respect to the polarizer 5. In this case, the polarization extraction angle of the analyzer 15 may be inclined in any direction. In the case where the analyzer 15 is set as described above and where the sample S does not have birefringent properties, a linear polarization component that has passed through the polarizer 5 and has been transmitted through the measurement target does not pass through the analyzer 15, whereas a linear polarization component that has been turned by 45 degrees by the birefringent properties of the sample S passes through the analyzer 15.

The detector 19 is composed of, for example, a two-dimensional CCD camera, and a detection signal thereof is inputted into and processed by a processing unit 23. Further, the processing unit 23, the lens drive mechanism 21, the drive stage 135, and the like are controlled by the control unit 25.

Figure 4A:
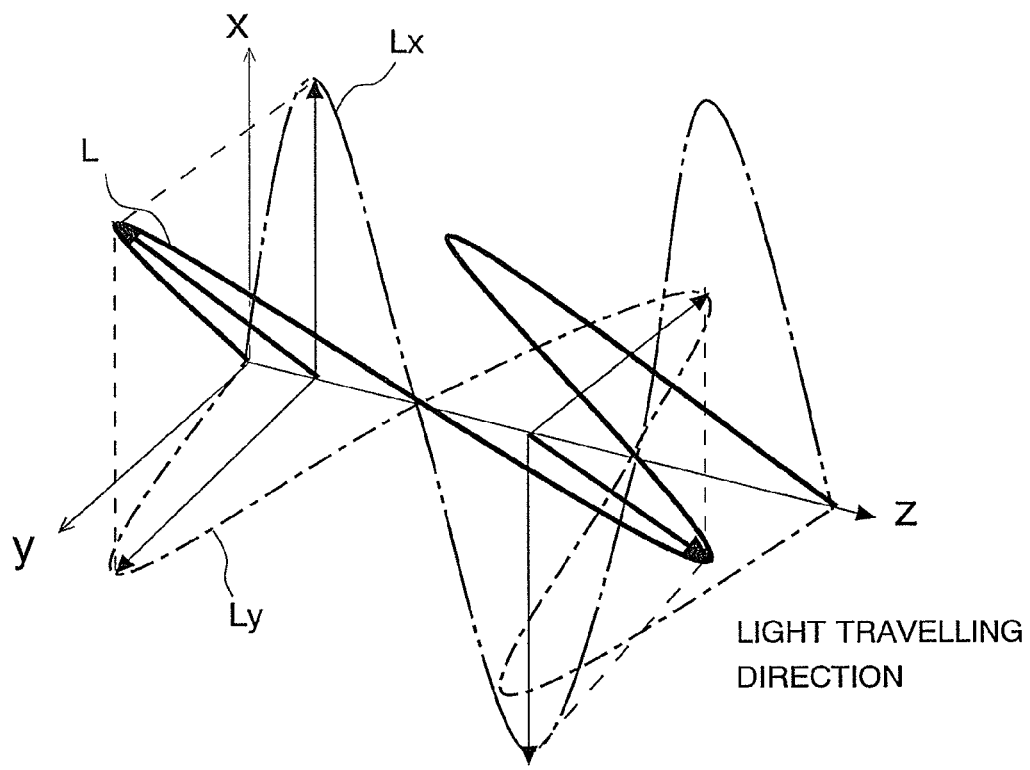
FIGS. 4A and 4B are graphs for describing a measurement principle of the optical characteristic measurement device according to the first embodiment.
Figure 4B:
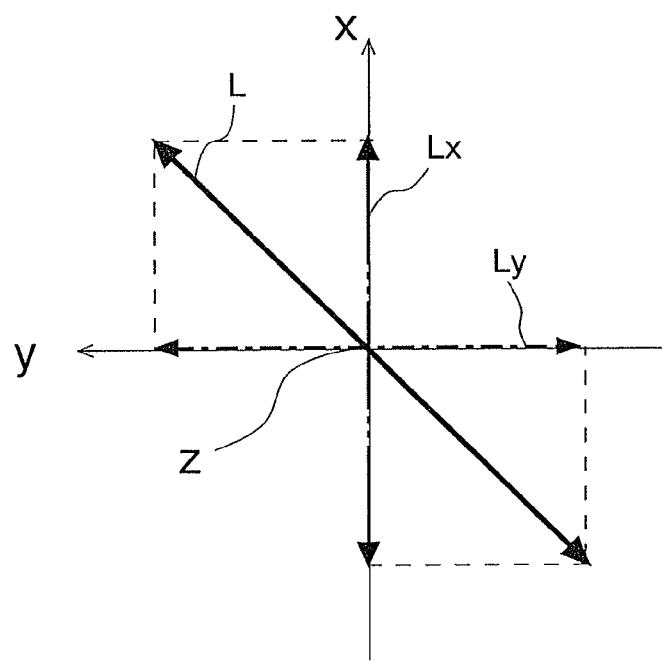

Next, a measurement principle of the optical characteristic measurement device 1 according to the present embodiment is described with reference to FIGS. 4A and 4B to FIGS. 10. In FIGS. 4A and 4B, the x axis represents the polarization direction of the first polarizing plate 9, and the y axis represents the polarization direction of the second polarizing plate 11. Further, the z axis is orthogonal to the x axis and the y axis, and represents a light travelling direction. In FIGS. 4A and 4B, oblique vibrations indicated by a solid line L represent observed linearly polarized light, that is, vibrations of the electric field vector of the linear polarization component that passes through the polarizer 5 and is delivered onto the sample S. When viewed in the light travelling direction, an electric field component linearly vibrates in an oblique direction at 45 degrees, and thus is referred to as linearly polarized light. Description is given of the case where the electric field component is subjected to vector decomposition into x-directional and y-directional orthogonal components. That is, an electric field component indicated by an alternate long and two short dashes line Lx and an electric field component indicated by an alternate long and short dash line Ly vibrate in synchronization with each other, and the linearly polarized light indicated by the solid line L is observed as the resultant synthetic vector.

Figure 5A:
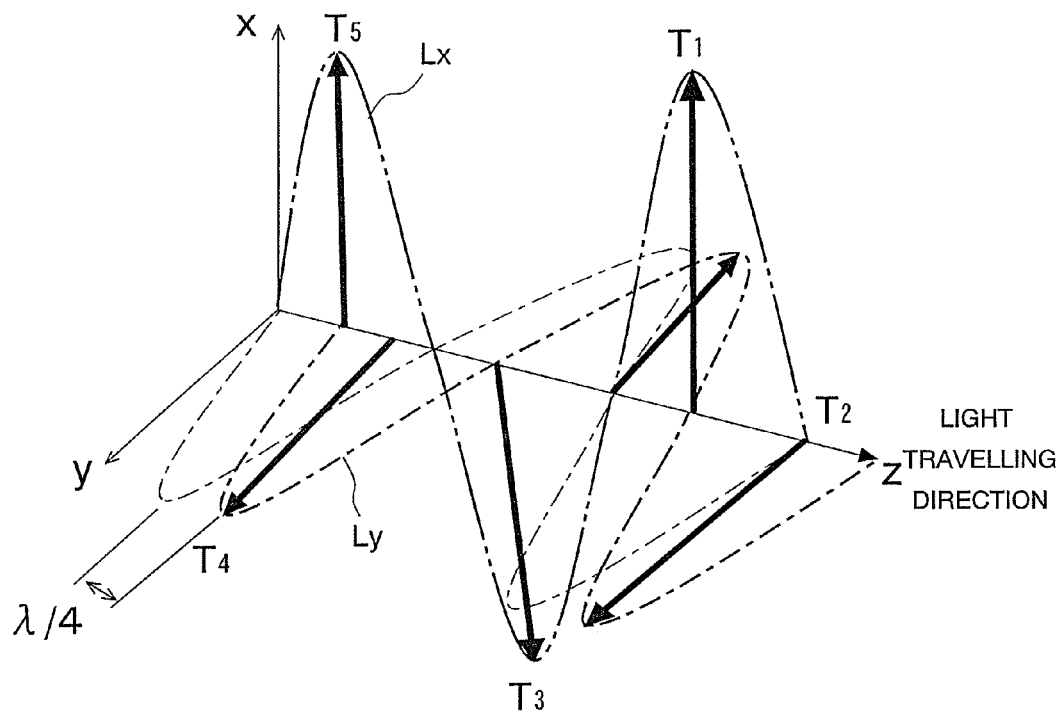
FIG. 5A is a graph showing a synthetic vector when a phase difference of λ/4 exists between the x-directional and y-directional electric field components.
Figure 5B:
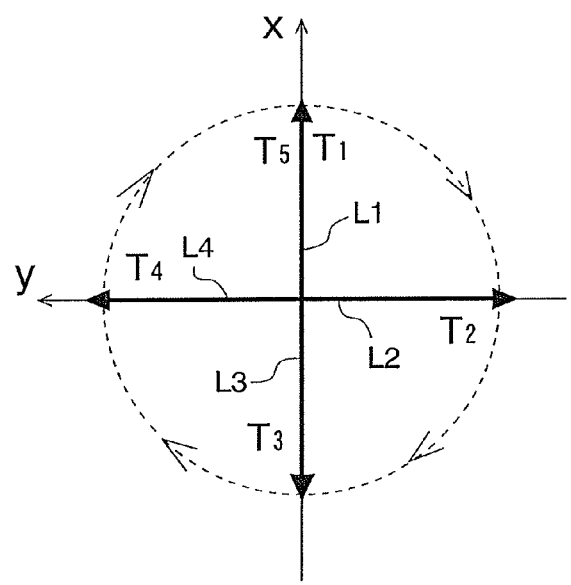
FIG. 5B is a graph showing the x-directional and y-directional electric field components and the synthetic vector, which are taken in the light travelling direction.

It is assumed that a phase difference between x-directional and y-directional electric field vibrations is, for example, $\lambda/4$ due to birefringent properties of a substance. In this case, as shown in FIG. 5A, the y-directional vector (alternate long and short dash line Ly) is at a node at a time point T1, and hence the synthetic vector is determined by only the x-directional component (alternate long and two short dashes line Lx). Conversely, the x-directional component (alternate long and two short dashes line Lx) is at a node at a time point T2, and hence the synthetic vector is determined by only the y-directional component (alternate long and short dash line Ly). In the case where the retardation of the orthogonally decomposed vector components is $\lambda/4$ as described above, the synthetic vector (solid lines L1 to L4) forms a so-called circularly polarized light, which turns when viewed in the light travelling direction (see FIG. 5B).

Figure 6A:
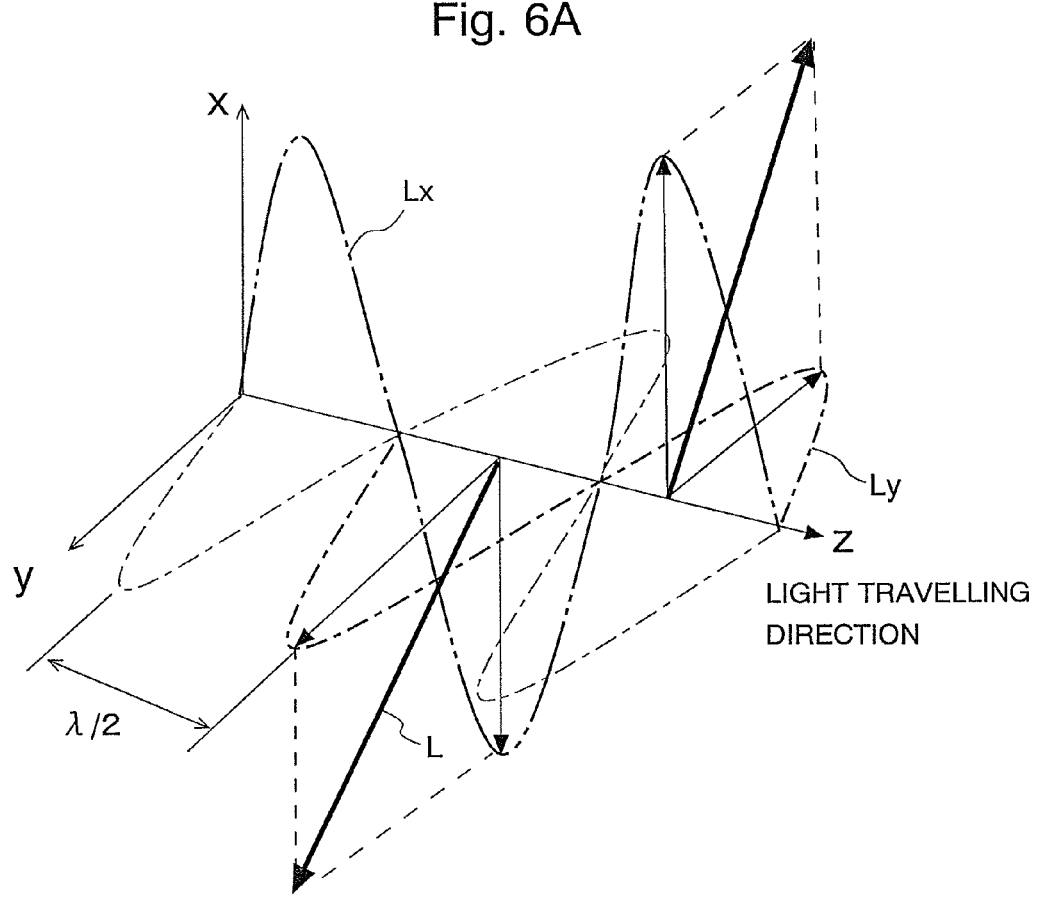
FIG. 6A is a graph showing a synthetic vector when a phase difference of λ/2 exists between the x-directional and y-directional electric field components.
Figure 6B:
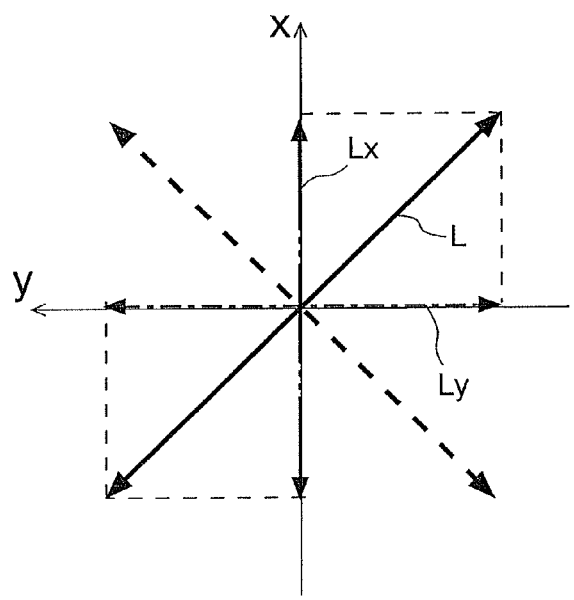
FIG. 6B is a graph showing the x-directional and y-directional electric field components and the synthetic vector, which are taken in the light travelling direction.

Meanwhile, as shown in FIG. 6A, in the case where a phase difference between x-directional and y-directional electric field vibrations is $\lambda/2$, the synthetic vector forms a linearly polarized light (indicated by a dotted line in FIG. 6B) orthogonal to the original linearly polarized light. At this time, in the case where the analyzer 15 is set in an open nicol state with respect to the polarizer 5, the synthetic vector cannot be transmitted through the analyzer 15.

Figure 7A:
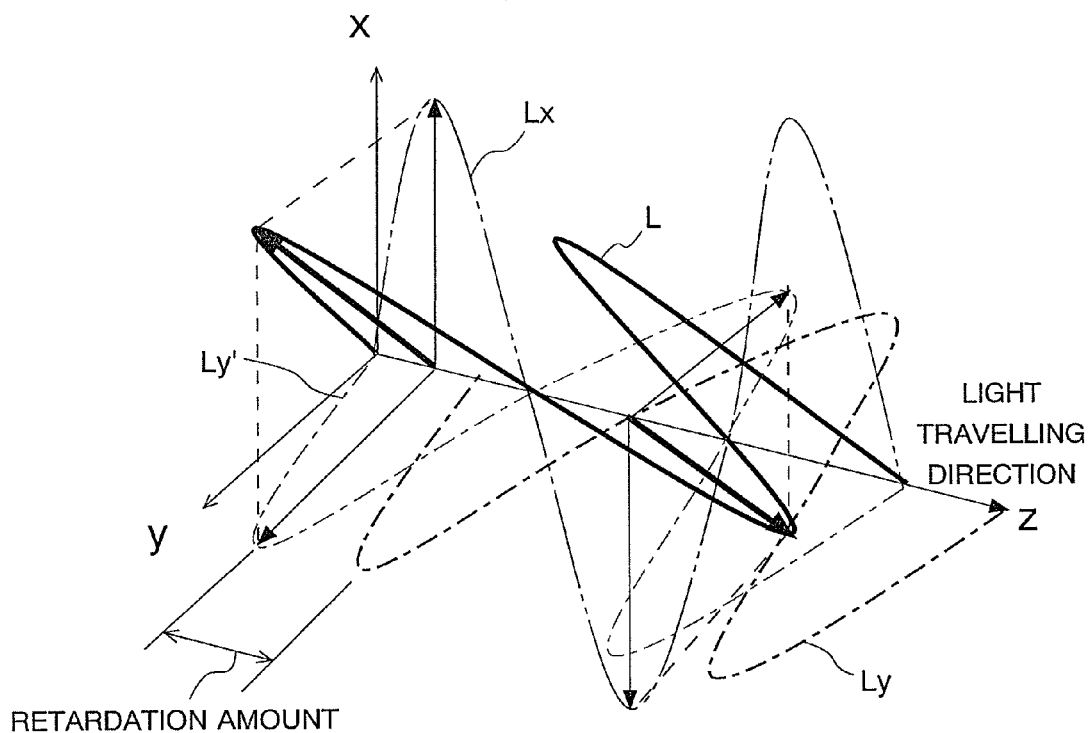
FIG. 7A is a graph showing a synthetic vector when a phase difference that cancels an unknown birefringent phase difference (retardation) given by a measurement target is provided between the x-directional and y-directional electric field components.
Figure 7B:
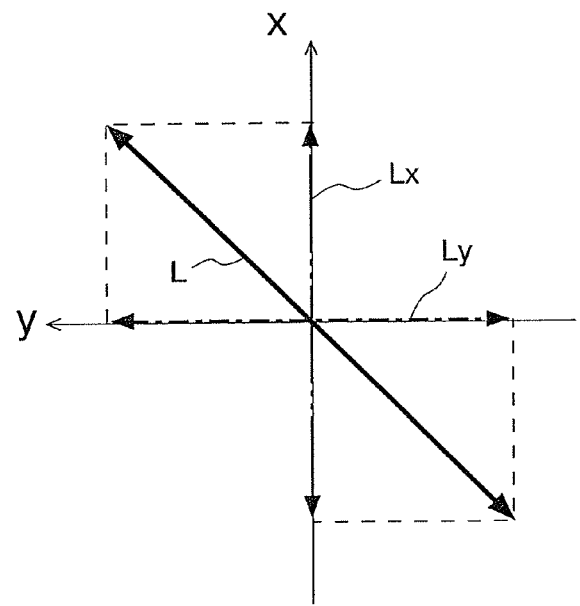
FIG. 7B is a graph showing the x-directional and y-directional electric field components and the synthetic vector, which are taken in the light travelling direction.

As shown in FIGS. 7A and 7B, it is assumed that an unknown retardation is given by the birefringent properties of the sample S to the two-directional electric field vector components Lx and Ly orthogonal to each other. A phase difference that cancels the retardation given by the sample S is given to such two-directional electric field components. In FIGS. 7A and 7B, the electric field vector components to which the retardation is given by the sample S are represented by Lx and Ly, and the electric field vector components to which the phase difference that cancels the retardation is given are represented by Lx and Ly'. Then, a synthetic vector L of the electric field vector components Lx and Ly' to which the phase difference that cancels the retardation is given returns to a linearly polarized light similar to the linearly polarized light delivered onto the sample S.

Figure 8:
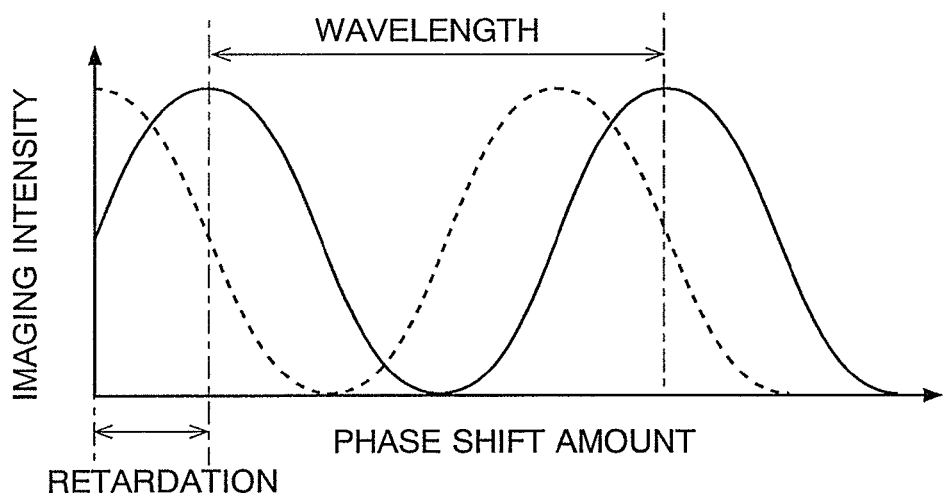
FIG. 8 is a graph showing a relation between a phase shift amount and an imaging intensity.
Figure 9:
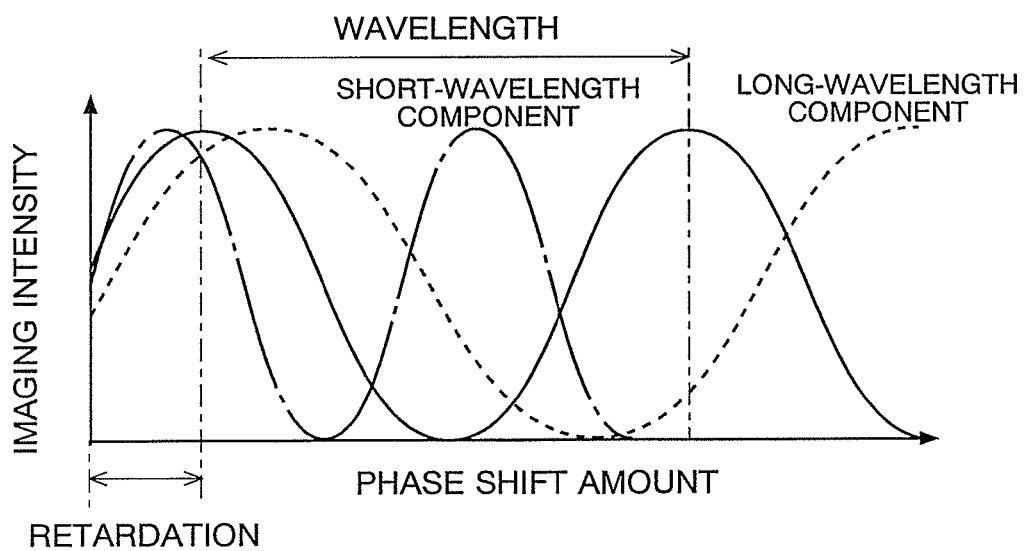
FIG. 9 is a graph showing a relation between a phase shift amount and an imaging intensity when a multi-wavelength light is delivered.
Figure 10:
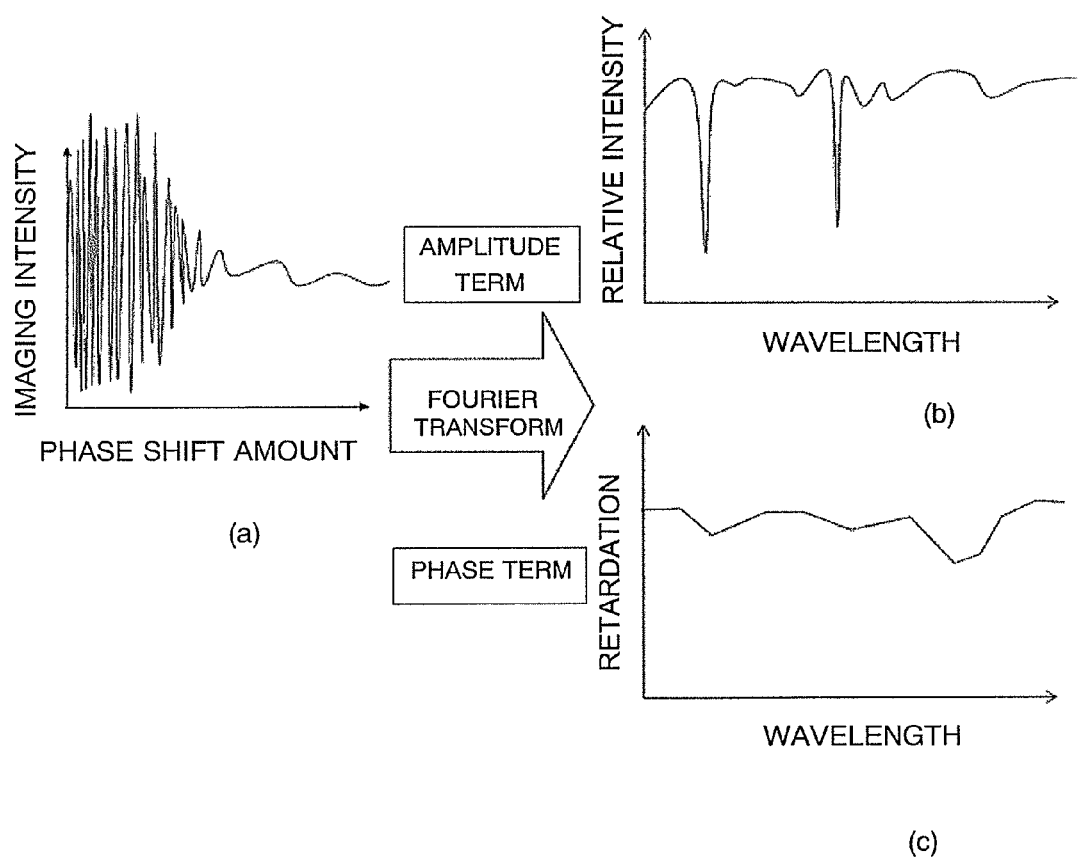
FIG. 10A is a synthetic waveform diagram of the imaging intensity of the multi-wavelength light.
FIG. 10B is a waveform diagram of a spectrum obtained by Fourier-transforming the synthetic waveform.
FIG. 10C is a diagram showing a retardation (birefringent phase difference) thereof.

In the present embodiment, a desired phase difference can be given by the phase shifter 13 between the first polarized light transmitted through the first polarizing plate 9 and the second polarized light transmitted through the second polarizing plate 11. Accordingly, a difference in optical path length between the first polarized light and the second polarized light is changed continuously and temporally by gradually moving the movable mirror unit 131, whereby a phase difference therebetween is changed. In this case, if a light from the light source 3 is a monochromatic light, as shown in FIG. 8, the imaging intensity of the light transmitted through the analyzer 15 that is set in an open nicol state with respect to the polarizer 5 becomes highest at a time point at which the amount of phase difference that cancels the retardation is given. If an amount of phase difference of $\lambda/2$ is further given to this amount of phase difference, the light becomes a linearly polarized light in the direction orthogonal to the direction of the linearly polarized light that is delivered onto the sample S from the polarizer 5, and hence the resultant light cannot be transmitted through the analyzer 15, so that the imaging intensity becomes lowest. If an amount of phase difference of $\lambda/2$ is further given, the phase difference becomes one wavelength ($\lambda$). Consequently, the light becomes again a linearly polarized light in the same direction as the direction of the linearly polarized light that is delivered onto the sample S from the polarizer 5, so that the imaging intensity becomes highest. In this way, the imaging intensity changes in such a sine-wave manner that brightness is inverted each time the amount of phase difference between the first polarized light and the second polarized light becomes one wavelength. If a multi-wavelength light is delivered, a difference in retardation amount per wavelength and a difference in wavelength appear as shown in FIG. 9.

As a result, as shown in FIG. 10A, a synthetic waveform, which is similar to an interferogram of Fourier-transform spectroscopy, can be observed. Because birefringent properties are not reflected in an interferogram of general Fourier-transform spectroscopy, in the obtained waveform, lights in all wavelength ranges strengthen each other at a position at which the amount of phase difference is zero. In contrast, in the present embodiment, if the retardation is different for each wavelength, as shown in FIG. 10A, a clear peak position cannot be observed in the obtained synthetic waveform. Because this synthetic waveform is formed by an overlap of sine waveforms of various frequencies, if the processing unit 23 mathematically performs Fourier transform thereon, an amplitude per wavelength and an amount of phase difference per wavelength can be analytically obtained at the same time. If a relative intensity is calculated from the amplitude term obtained through the Fourier transform, spectral characteristics that are a relative intensity per wavelength can be obtained (FIG. 10B), similarly to Fourier-transform spectroscopy. Further, a retardation per wavelength can be acquired from the phase difference term calculated through the Fourier transform (FIG. 10C). That is, spectral characteristics and birefringent properties can be measured at the same time.

The optical system in the present embodiment is the imaging optical system, and hence two-dimensional measurement of spectral characteristics and birefringent properties is possible. Further, the retardation of an object light reflected at a given depth can be obtained by shifting the focal point of the objective lens 7 in the depth direction by means of the lens drive mechanism 21. Because the retardation is obtained as the product of the index of birefringence and the path length of the object light, if the depth at which the object light is reflected is determined, the index of birefringence can be calculated from the retardation.

Figure 11:
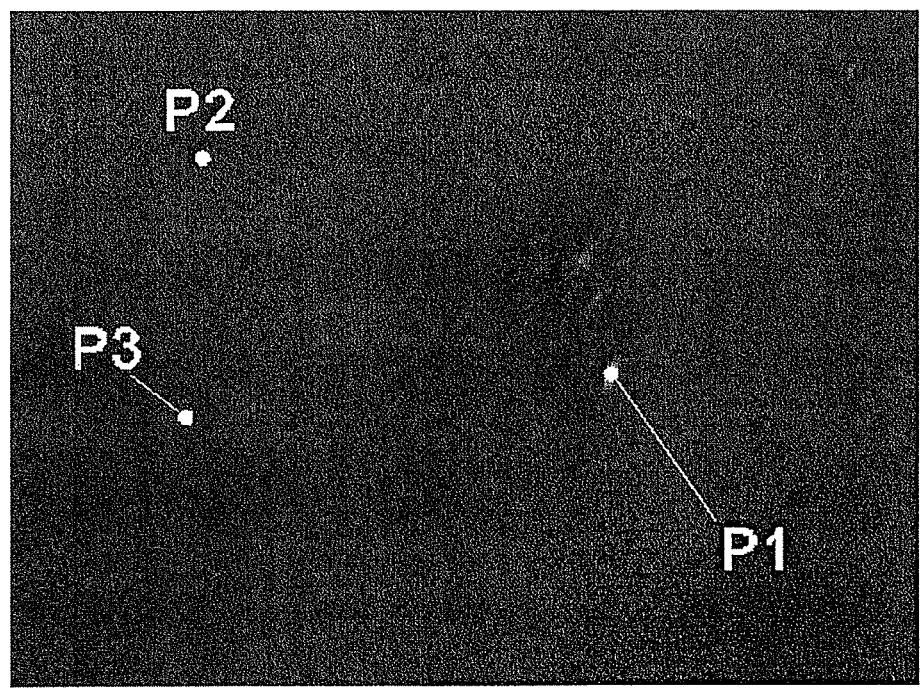
FIG. 11 is an observation image of a stone material obtained using an oblique illumination interferometer.

With the optical system of the optical characteristic measurement device 1 shown in FIG. 1 being replaced with an oblique illumination optical system, spectral characteristics of a stone material made of granite were measured, and the obtained results are shown in FIG. 11 to FIG. 14. Compared with a vertical epi-illumination optical system, the amount of light taken using the oblique illumination optical system remarkably decreased, but bright portions (denoted by symbols P1 to P3) were partially found as shown in FIG. 11. Because the surface of the stone material used for observation was mirror-polished, these bright portions P1 to P3 can be regarded as portions at which diffusely reflected components from the inside of the stone material were observed.

Figure 12:
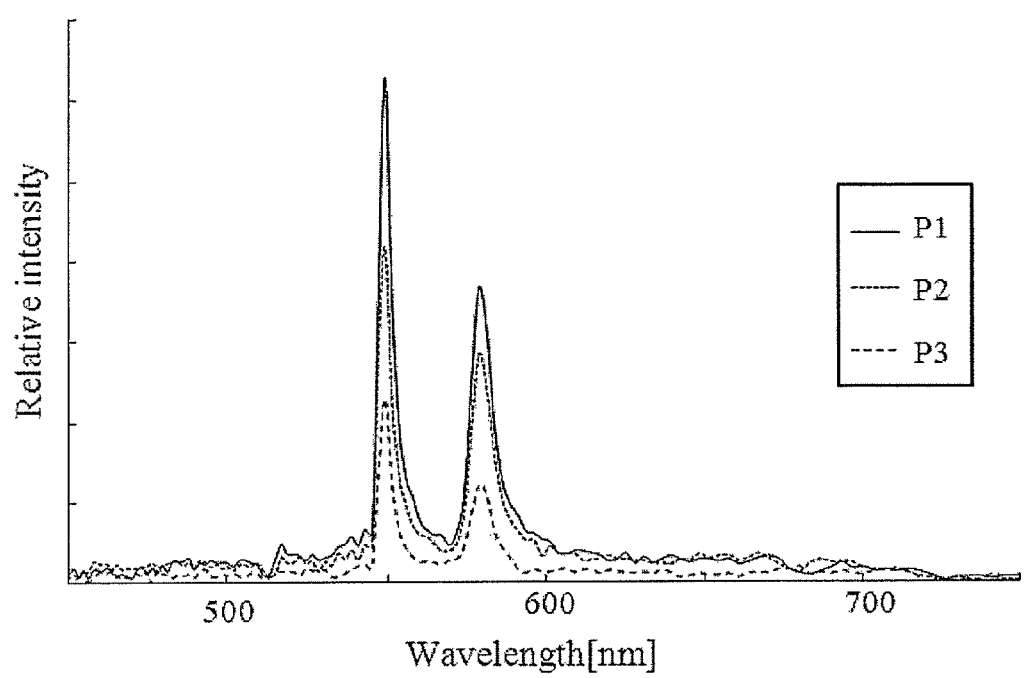
FIG. 12 is a graph showing a spectrum of the stone material.
Figure 13:
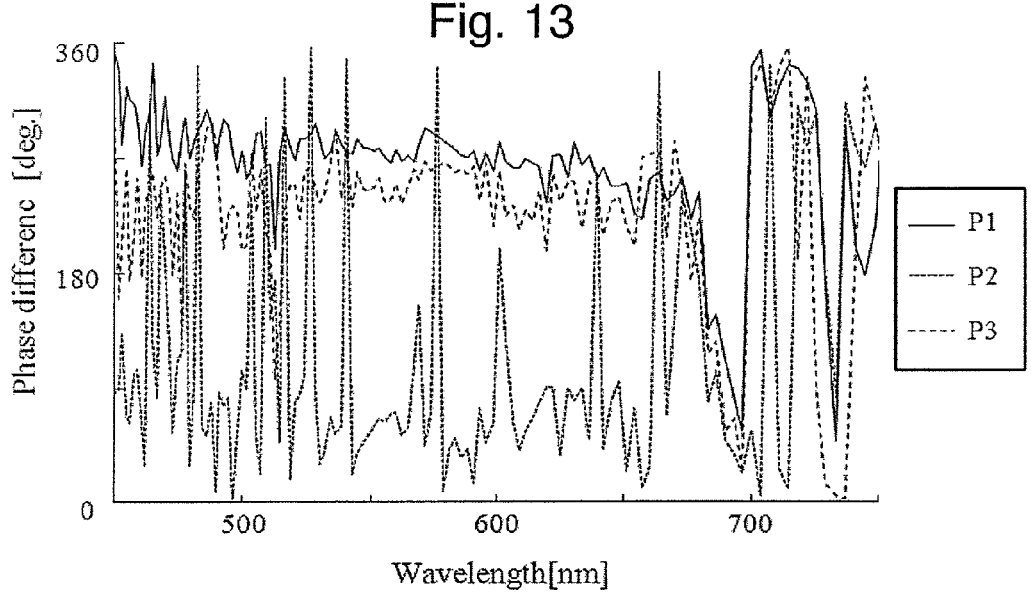
FIG. 13 is a graph showing a relation between a retardation amount of the stone material and a wavelength.

In view of the above, spectral data and phase data were obtained for the three portions P1 to P3 shown in FIG. 11. The results thereof are shown in FIG. 12 and FIG. 13. FIG. 12 shows a spectrum in which the horizontal axis represents the wavelength (nm) and the vertical axis represents the intensity. FIG. 13 is a graph in which the horizontal axis represents the wavelength (nm) and the vertical axis represents the phase difference (deg.), and the retardation amount is plotted in this graph. As shown in FIG. 12, although the light emission intensities at the three portions P1 to P3 were significantly different, an emission line spectrum of the light source could be found for all the three portions.

Meanwhile, as shown in FIG. 13, the retardation amount significantly changed at wavelengths other than a peak wavelength of the light source spectrum, and was relatively stable around the peak wavelength (540 to 560 nm). The reason why the retardation amount significantly changed at wavelengths other than the peak wavelength is considered to be that phase measurement is unstable when the light emission intensity is extremely low. Note that, for the portions P2 and P3, a characteristic reflection intensity was observed around a wavelength of 700 nm.

Figure 14:
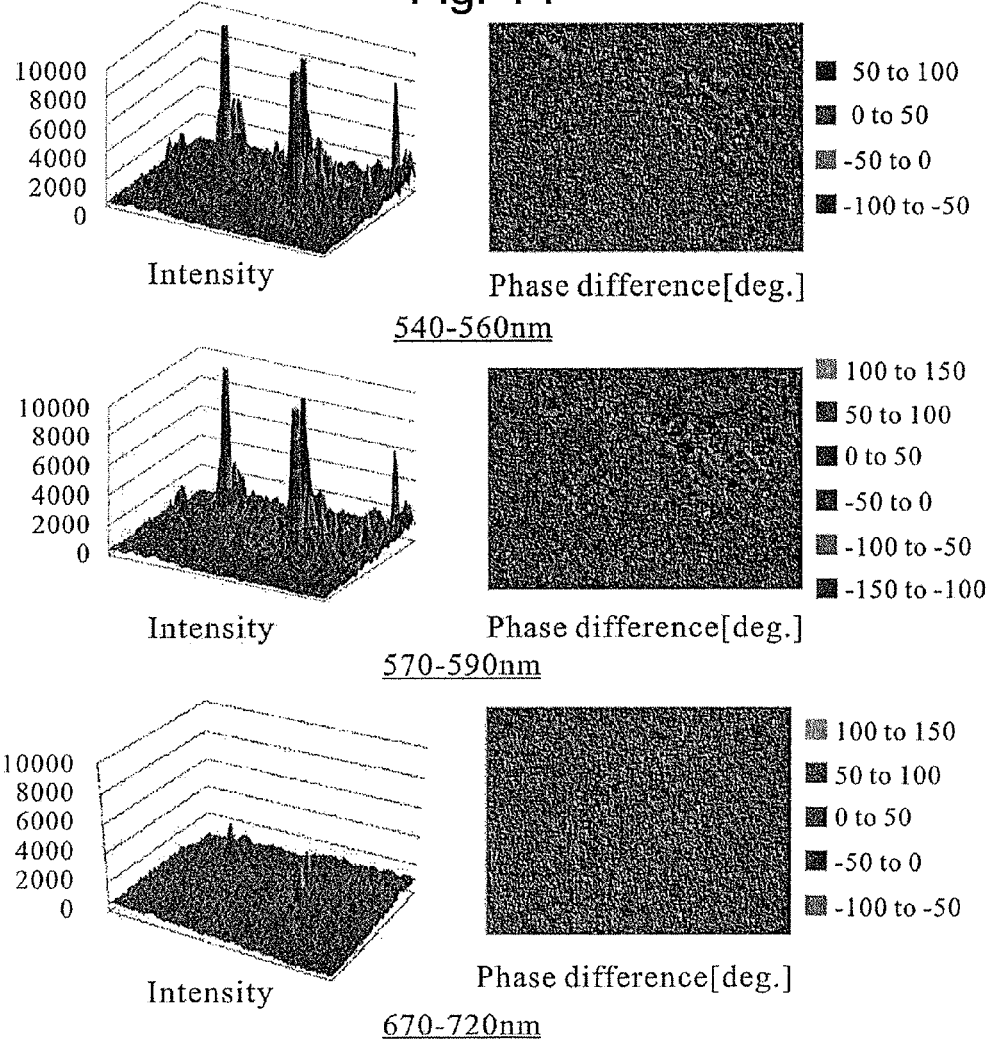
FIG. 14 is diagrams showing intensity distributions and phase distributions of the stone material in particular wavelength ranges.
Figure 15:
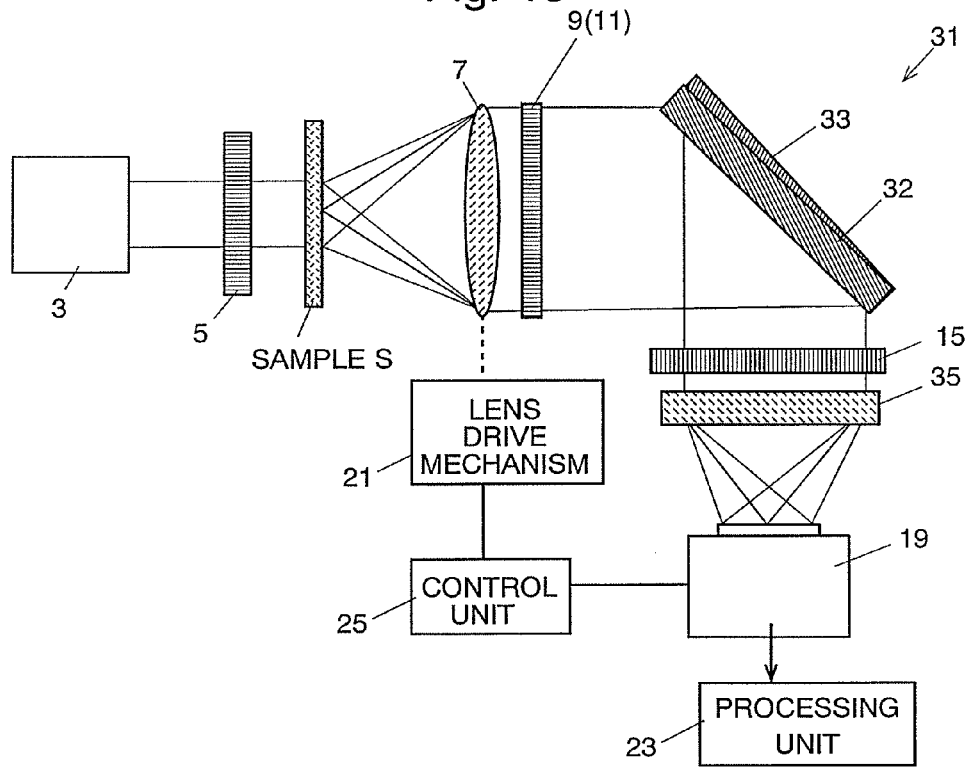
FIG. 15 is a view showing a schematic overall configuration of an optical characteristic measurement device according to a second embodiment of the present invention.

Next, intensity distributions and phase distributions in wavelength ranges of 540 to 560 nm, 570 to 590 nm, and 670 to 720 nm each having a characteristic spectrum are shown in FIG. 14. With reference to FIG. 14, a characteristic phase distribution was measured in the wavelength range of 540 to 560 nm, and a characteristic intensity distribution was measured in the wavelength range of 670 to 720 nm. This proves that even the spectral characteristic measurement device 1 using an oblique illumination method is capable of measuring both spectral characteristics and birefringent properties of internally reflected components of the stone material at the same time.

Second Embodiment

FIG. 15 to FIG. 18 show the optical characteristic measurement device 1 according to a second embodiment. The optical characteristic measurement device 1 according to the second embodiment is significantly different from that according to the first embodiment in the configurations of the phase shifter and the imaging optical system. Note that, in FIG. 16, the analyzer 15 arranged upstream of an imaging lens 35 forming the imaging optical system is omitted for convenience sake.

In the second embodiment, the linear polarization component that has been emitted from the light source 3 and transmitted through the polarizer 5 is delivered onto a linear measurement area S1 of the sample S. The light ray that has been delivered onto the measurement area S1 of the sample S and transmitted through the measurement area S1 enters the objective lens 7, and is converted into parallel beams. Then, the parallel beams pass through the first polarizing plate 9 and the second polarizing plate 11, and reach a phase shifter 31.

The phase shifter 31 includes a reference mirror unit 32, an oblique mirror unit 33, and holders (not shown) for respectively holding the mirror units 32 and 33. The surfaces (reflection surfaces) of the reference mirror unit 32 and the oblique mirror unit 33 are optically flat, and are rectangular optical mirror surfaces that can reflect lights in wavelength ranges to be measured by the device 1. Further, the sizes of the reflection surfaces of the reference mirror unit 32 and the oblique mirror unit 33 are substantially the same.

In the case where the texture of an object is one-sided, a light (object light) generated at each of bright points that optically constitute the object travels only in a specific direction. Hence, the light amount distribution of the parallel beams that reach the phase shifter 31 may be uneven. This might prevent the light amount distribution on a light-receiving surface 19a of the detector 19 that is the imaging plane from being even. In contrast, in the case where the texture of an object is relatively uneven, object lights that reach the phase shifter 31 have an even light amount distribution thereon. In the following description, suppose that the texture of the sample S is relatively uneven, that the beams that reach the phase shifter 31 have an even light amount distribution thereon, and that the same amount of beam is delivered onto the reflection surfaces of the reference mirror unit 32 and the oblique mirror unit 33.

In the present embodiment, the objective lens 7, the first polarizing plate 9, and the second polarizing plate 11 correspond to a division optical system, and the phase shifter 31 corresponds to a phase changer.

Note that, in the following description, the beam that reaches the reflection surface of the reference mirror unit 32 of the phase shifter 31 from the first polarizing plate 9 and is reflected thereon to reach the analyzer 15 is also referred to as reference beam, and the beam that reaches the reflection surface of the oblique mirror unit 33 of the phase shifter 31 from the second polarizing plate 11 and is reflected thereon to reach the analyzer 15 is also referred to as oblique beam.

The reference mirror unit 32 is arranged such that its reflection surface is inclined by 45 degrees, for example, with respect to the optical axis of the parallel beam from the objective lens 7. Further, the oblique mirror unit 33 is arranged such that its reflection surface is inclined at $(45+\Delta\theta)$ degrees with respect to the optical axis of the parallel beam from the objective lens 7. This oblique positioning of the reference mirror unit 32 and the oblique mirror unit 33 with respect to the parallel beams from the objective lens 7 can eliminate a beam splitter for dividing the beam. Although the objective lens 7 is used in the present embodiment, this function can also be realized by using a reflection optical system. Since this configuration can eliminate any influence of dispersion, spectral characteristics across a wide band can be measured.

Further, the inclination angle, $\Delta\theta$, of the oblique mirror unit 33 with respect to the reference mirror unit 32 is determined by optical conditions, such as the magnification of the imaging optical system, the measuring wavelength range, and the wavenumber resolution. For example, consider the case where the measuring wavelength is from the visible range to the near-infrared range (400 to 1,000 nm). In order to obtain the wavelength resolution of $\lambda^2/\Delta^2=5$ nm, since the central wavelength is $\lambda=700$ nm, the phase shift amount is $\Delta\lambda=100$ µm. In the case where a CCD camera is used as the detector 19 (light-receiving element), the number of pixels in approximately one line is about 500. Therefore, if the phase shift amount per line is 100 µm, the phase difference amount per pixel is 200 nm, which enables measurement of the wavelength up to 400 nm by a sampling theorem. Since the measuring wavelength is from the visible range to the near-infrared range (400 to 1,000 nm) as described above, if the phase difference amount per pixel is 200 nm, the sampling theorem on the short wavelength side is satisfied.

Further, the maximum distance between the reference mirror unit 32 and the oblique mirror unit 33 may be set to be half the phase shift amount (100 µm) per line of a general CCD camera, that is, may be set to 50 µm/2). For example, in the case where the length along the optical path direction (the inclined direction of each mirror unit) of each of the mirror units 32 and 33 is approximately 3 mm, the inclination angle is approximately 1 degree.

Further, particularly in a long-wavelength region for mid-infrared lights, not only the interference intensity change of an interferogram, but also the envelope of the interference intensity change must be acquired in a long-stroke phase shift region. This is also understood from the principle of Fourier spectroscopy that a large phase shift amount is required to increase the wavenumber resolution. Detecting the envelope of the interferogram for a long stroke requires that the oblique mirror unit 33 has a large inclination angle. In this case, an inclination change mechanism for two modes, for example, may be provided to detect the interference intensity change of the interferogram and to detect the envelope. In the case where the envelope is measured in the mid-infrared region, since the required phase shift amount is approximately 50 mm, for example, the length along the optical path direction may be lengthened to 100 mm, and the inclination angle may be set to 2.9 degrees, for example.

The reference beam and the oblique beam that have reached the phase shifter 31 and have been respectively reflected on the reflection surfaces of the reference mirror unit 32 and the oblique mirror unit 33 are transmitted through the analyzer 15, and then enter the imaging lens 35. In the present embodiment, the imaging lens 35 is made of a cylindrical lens, and is arranged such that its convex surface faces the phase shifter 31 and its plain surface faces the light-receiving surface 19a of the detector 19. The light-receiving surface 19a of the detector 19 is located on the imaging plane of the imaging lens 35. Hence, the reference beam and the oblique beam that have been emitted from a bright point in the measurement area S1, have been reflected on the reflection surfaces of the reference mirror unit 32 and the oblique mirror unit 33, and then have entered the imaging lens 35 are converged only in one direction by the imaging lens 35, and are focused on a single straight line on the light-receiving surface 19a of the detector 19, to thereby form an image. In the present embodiment, suppose that the imaging lens 35 is arranged such that the direction (which is indicated by an arrow B in FIG. 16) in which its convex surface is curved is parallel to the direction of the measurement area S1. Because of this configuration, the reference beam and the oblique beam that have entered the imaging lens 35 are focused on the straight line that is on the light-receiving surface 19a and is orthogonal to the measurement area S1.

The reflection surface of the reference mirror unit 32 and the reflection surface of the oblique mirror unit 33 are provided so as to be relatively parallel to each other to the degree to which the light-focusing positions of these two beams are not displaced in relation to each other on the light-receiving surface 19a (imaging plane) of the detector 19 (two-dimensional CCD camera).

A measurement principle of the present embodiment is described. The description is based on the following optical model. The reference beam is focused by the imaging lens 35, as waves having the same phase on a straight line on the light-receiving surface 19a of the detector 19. At this time, the oblique beam is focused as waves whose phase gradually differs from that of the reference beam on a straight line on the light-receiving surface 19a.

As described above, the beam transmitted through the measurement area S1 of the sample S passes through the objective lens 7, the first polarizing plate 9, and the second polarizing plate 11, and reaches the surfaces of the reference mirror unit 32 and the oblique mirror unit 33 of the phase shifter 31. At this time, the beam is vertically divided into two, and the two beams respectively reach the surfaces of the reference mirror unit 32 and the oblique mirror unit 33. Note that the surface areas of the mirror units 32 and 33 are set such that the amount of light of the beam that has reached the surface of the reference mirror unit 32 (i.e. the reference beam) is substantially the same as that of the beam that has reached the surface of the oblique mirror unit 33 (i.e. the oblique beam). Alternatively, a dark filter may be set on one or both of the optical paths of the reference beam and the oblique beam so as to adjust the relative light amount difference and thus equalize their amounts of light.

Figure 17A:
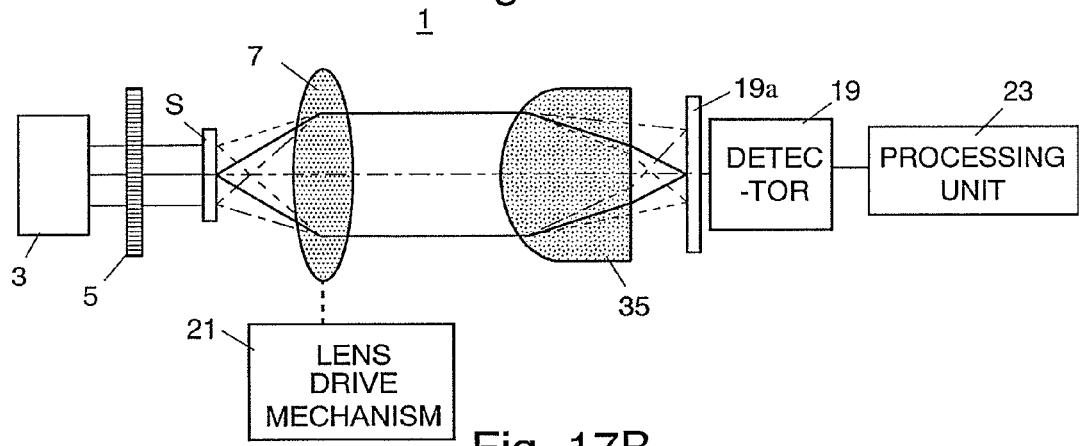
FIGS. 17A and 17B are side views each showing a state where measurement lights are focused on a light-receiving surface by an imaging lens in the second embodiment.
Figure 17B:
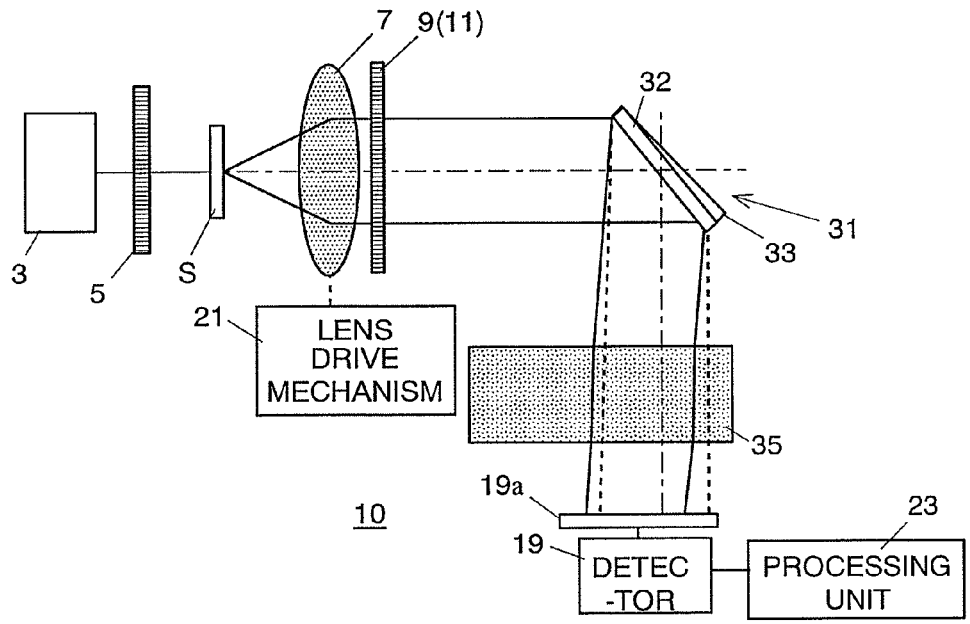
Figure 18:
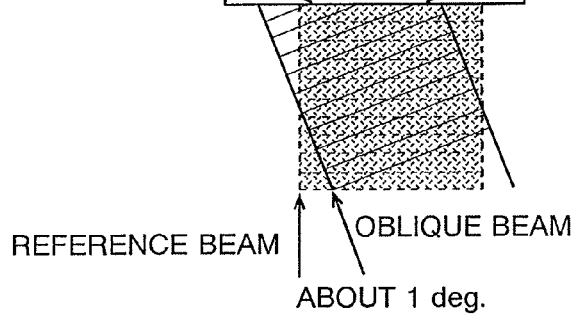
FIG. 18 is a top view showing the state where the measurement lights are focused on the light-receiving surface by the imaging lens in the second embodiment.

The beams that have been reflected on the surfaces of the reference mirror unit 32 and the oblique mirror unit 33 enter the imaging lens 35 as the reference beam and the oblique beam. The reference beam and the oblique beam are focused on a single straight line on the light-receiving surface 19a of the detector 19, to thereby form an interference image. Since the reference beam passes through the imaging lens 35 and is focused as waves having the same phase on the light-receiving surface 19a that is the imaging plane, the wavefronts of the reference beam are parallel to the light-receiving surface 19a of the detector 19, as shown in FIGS. 17A and 17B. Meanwhile, since the oblique beam enters the imaging lens 35 with its optical axis being inclined by $2\times\Delta\theta°$ with respect to the optical axis of the reference beam, the wavefronts of the oblique beam are a little inclined with respect to the light-receiving surface 19a.

As just described, the wavefronts of the oblique beam are inclined with respect to those of the reference beam. Therefore, in the light interference area between the reference beam and the oblique beam, the optical path length difference between the two beams gradually changes (gradually becomes larger from right to left in FIGS. 17A and 17B). Specifically, in the first embodiment, the movable mirror unit 131 is gradually moved, whereby a continuously changing phase difference is provided between the first polarized light and the second polarized light. Meanwhile, in the present embodiment, the reference mirror unit 32 and the oblique mirror unit 33 are arranged such that the mirror unit 33 is inclined with respect to the mirror unit 32, whereby a continuously changing phase difference is provided between the first polarized light and the second polarized light. Moreover, the phase difference temporally changes in the first embodiment, whereas the phase difference spatially changes in the second embodiment.

Since the beam emitted from the measurement area S1 includes lights having a variety of wavelengths (and the initial phases of lights having respective wavelengths are not always the same), the optical path length difference between the reference beam and the oblique beam continuously changes in the interference area. Further, due to a difference in retardation per wavelength, a synthetic waveform as shown in FIG. 10A, which is similar to an interferogram, can be observed.

Figure 16:
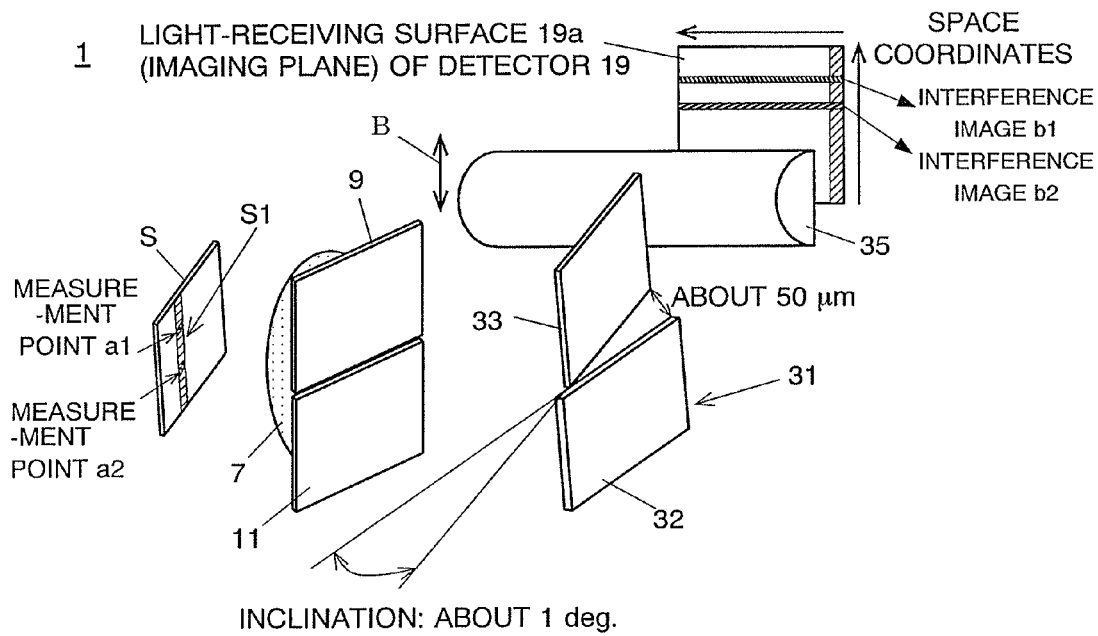
FIG. 16 is a view showing an arrangement of optical elements from a measurement target to an imaging plane in the optical characteristic measurement device according to the second embodiment.

For example, as shown in FIG. 16, the beam emitted from a bright point (measurement point) a1 in the measurement area S1 is focused on a straight line on the light-receiving surface 19a (imaging plane) to thereby form a linear interference image b1, while the beam emitted from a bright point (measurement point) a2 is focused on a straight line on the light-receiving surface 19a to thereby form a linear interference image b2. Each of the synthetic waveforms of the interference images b1 and b2 is obtained from the intensity of the received light of a plurality of pixels aligned along each interference image. Accordingly, in the second embodiment, in FIG. 10A, the horizontal axis represents the pixel number of the pixels of the detector 19 that are aligned along the linear interference image, and the vertical axis represents the imaging intensity (the intensity of received light of each pixel). If the pixel number is converted by the phase shift amount for each pixel, the synthetic waveform in which the horizontal axis represents the phase shift amount can be obtained.

The processing unit 23 Fourier-transforms the obtained synthetic waveform, and thus can acquire spectral characteristics, which show the relative intensity per wavelength of the light emitted from each bright point in the measurement area S1, and a retardation per wavelength. If spectral characteristics can be obtained using all the pixels of the detector 19, one-dimensional spectral measurement of the measurement area S1 can be realized. If the measurement area S1 onto which a linearly polarized light is delivered is scanned, two-dimensional spectral measurement of the object to be measured S can be realized. If the measurement area S1 is scanned and the focal plane (the plane including the focal point) is shifted by moving the objective lens 7, three-dimensional spectral measurement can be realized.

Third Embodiment

Figure 19:
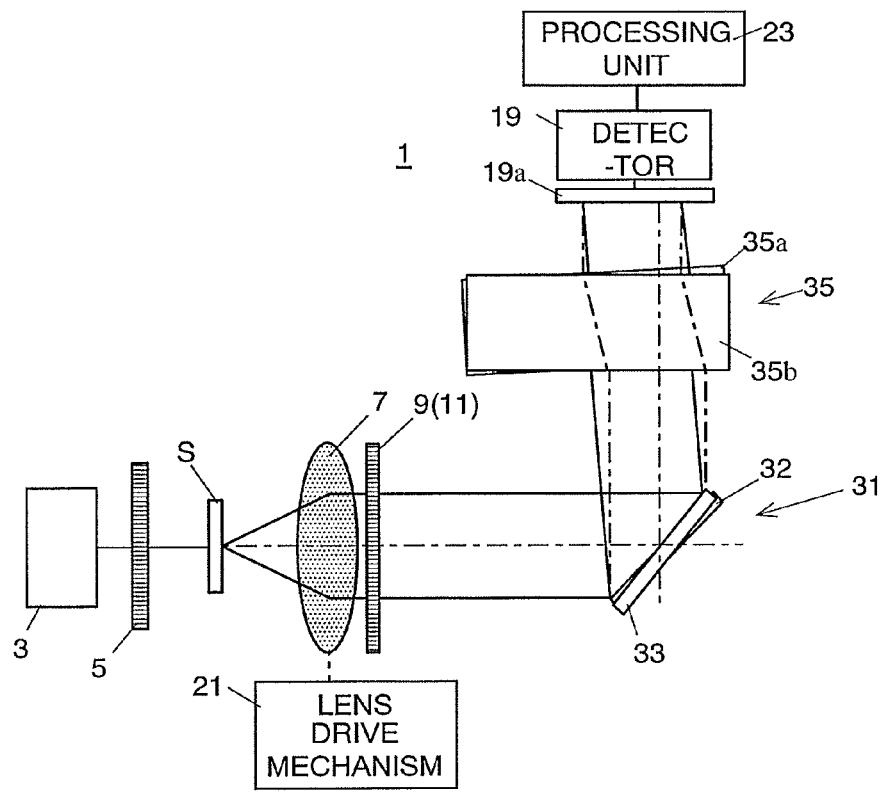
FIG. 19 is a view showing a schematic overall configuration of an optical characteristic measurement device according to a third embodiment of the present invention.
Figure 20:
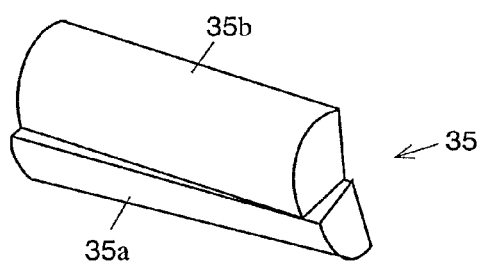
FIG. 20 is a perspective view of an imaging lens in the third embodiment.
Figure 21:
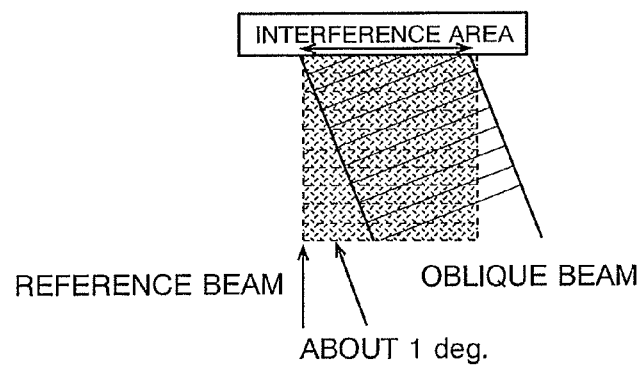
FIG. 21 is a view showing an interference image between a reference beam and an oblique beam in the third embodiment.

FIG. 19 to FIG. 21 show a third embodiment of the present invention. As shown in FIG. 19 and FIG. 20, in the spectral characteristic measurement device 1 of the present embodiment, the imaging lens 35 is divided into a reference lens unit 35a and an oblique lens unit 35b. The reference beam that has been reflected on the reference mirror unit 32 enters the reference lens unit 35a, while the oblique beam that has been reflected on the oblique mirror unit 33 enters the oblique lens unit 35b. The reference lens unit 35a and the oblique lens unit 35b each have a shape obtained by evenly dividing the imaging lens 35 of the second embodiment into two, and are arranged such that the inclination of the optical axis of one of the reference beam and the oblique beam with respect to the optical axis of the other thereof is maintained, while the optical axis of the other thereof is shifted along a linear interference image formed on the light-receiving surface 19a (imaging plane) of the detector 19. In other words, the reference lens unit 35a and the oblique lens unit 35b function as an imaging optical system and an optical axis changer.

This configuration can increase the area (i.e. interference area) in which the reference beam overlaps with the oblique beam on the light-receiving surface 19a, as shown in FIG. 21.

Fourth Embodiment

FIG. 22 shows a fourth embodiment of the present invention. In the fourth embodiment, a monochromatic light converter 41, such as a fluorescent plate, for converting a light intensity into a monochromatic light is set at the position of the imaging plane in the second embodiment, and a cylindrical lens 43 is arranged at the position of the monochromatic light converter 41 that is considered as an object plane. Then, the detector 19 is arranged such that its light-receiving surface 19a is located on the optical Fourier-transform plane of the cylindrical lens 43. The cylindrical lens 43 is arranged such that the direction of its non-curved portion is orthogonal to the direction in which a linear interference image extends.

In the fourth embodiment, the interference image of the reference beam and the oblique beam that have been transmitted through the imaging lens 35 is converted into a spatial brightness intensity distribution by the monochromatic light converter 41. Then, the intensity distribution is optically Fourier-transformed by the cylindrical lens 43, and an optical spectrum is formed on the imaging plane in real time. Since the light-receiving surface 19a of the detector 19 is located on the Fourier-transform plane of the cylindrical lens 43, optically obtaining the light intensity distribution of the optical spectrum enables an acquisition of the same spectral characteristics and birefringent properties as in the case where the synthetic waveform obtained in the second embodiment is mathematically Fourier-transformed. That is, in the present embodiment, the spectral characteristics and the birefringent properties can be directly obtained without the need to perform a Fourier-transform operation, which enables the spectral characteristics to be obtained in a shorter time. Note that, in the fourth embodiment, the monochromatic light converter 41 and the cylindrical lens 43 form a spectral optical system.

The present invention is not limited to the aforementioned embodiments, and can be changed as appropriate. For example, in the first embodiment, the analyzer 15 arranged upstream of the imaging lens 17 may be arranged downstream of the imaging lens 17. If the analyzer 15 is arranged downstream of the imaging lens 17, however, imaging characteristics deteriorate, and hence it is preferable to arrange the analyzer 15 upstream of the imaging lens, as in the first embodiment.

EXPLANATION OF NUMERALS

1 . . . Optical Characteristic Measurement Device
3 . . . Light Source
5 . . . Polarizer
7 . . . Objective Lens
9 . . . First Polarizing Plate
11 . . . Second Polarizing Plate
13, 31 . . . Phase Shifter
15 . . . Analyzer
17 . . . Imaging Lens
19 . . . Detector
19a . . . Light-Receiving Surface 21 ... Lens Drive Mechanism
23 ... Processing Unit
25 ... Control Unit
32 ... Reference Mirror Unit
33 ... Oblique Mirror Unit
35 ... Imaging Lens
35a ... Reference Lens Unit
35b ... Oblique Lens Unit
41 ... Monochromatic Light Converter
43 ... Cylindrical Lens
131 ... Movable Mirror Unit
132 ... Fixed Mirror Unit

The invention claimed is:

1. An optical characteristic measurement device comprising:
   a) a division optical system for directing a light emitted from an object to be measured, on which a linearly polarized light is incident, to a first polarizing plate and a second polarizing plate;
   b) an analyzer for allowing a synthetic light in a predetermined polarization direction to be transmitted therethrough, the synthetic light being made of a first polarization component transmitted through the first polarizing plate and a second polarization component transmitted through the second polarizing plate;
   c) an imaging optical system for directing the synthetic light transmitted through the analyzer to a single point so as to thereby form an interference image;
   d) a detection unit for detecting a light intensity of the interference image;
   e) a phase difference changer for changing a difference in optical path length between the first polarization component and the second polarization component that respectively travel from the first polarizing plate and the second polarizing plate to the analyzer, to thereby change a phase difference between the first polarization component and the second polarization component; and
   f) a processing unit for Fourier-transforming data of a change in light intensity detected by the detection unit along with the change in phase difference, to thereby acquire an amplitude per wavelength and a birefringent phase difference per wavelength of the light emitted from the object to be measured.

2. An optical characteristic measurement device comprising:
   a) a division optical system for directing a light emitted from an object to be measured, on which a linearly polarized light is incident, to a first polarizing plate and a second polarizing plate;
   b) an analyzer for allowing a synthetic light in a predetermined polarization direction to be transmitted therethrough, the synthetic light being made of a first polarization component transmitted through the first polarizing plate and a second polarization component transmitted through the second polarizing plate;
   c) an imaging optical system for focusing the synthetic light transmitted through the analyzer on a single straight line that extends in a direction different from those of optical axes of the first polarization component and the second polarization component, to thereby form a linear interference image;
   d) a phase changer for giving a continuous optical path length difference distribution between the first polarization component and the second polarization component that respectively travel from the first polarizing plate and the second polarizing plate to the analyzer, to thereby give a continuous phase change between the first polarization component and the second polarization component;
   e) a detection unit for detecting a light intensity distribution of the linear interference image along a direction in which the interference image extends; and
   f) a processing unit for Fourier-transforming data indicating the light intensity distribution of the interference image detected by the detection unit, to thereby acquire an amplitude per wavelength and a birefringent phase difference per wavelength of the light emitted from the object to be measured.

3. An optical characteristic measurement device comprising:
   a) a division optical system for directing a light emitted from an object to be measured, on which a linearly polarized light is incident, to a first polarizing plate and a second polarizing plate;
   b) an analyzer for allowing a synthetic light in a predetermined polarization direction to be transmitted therethrough, the synthetic light being made of a first polarization component transmitted through the first polarizing plate and a second polarization component transmitted through the second polarizing plate;
   c) an imaging optical system for focusing the synthetic light transmitted through the analyzer on a single straight line that extends in a direction different from those of optical axes of the first polarization component and the second polarization component, to thereby form a linear interference image;
   d) a phase changer for giving a continuous optical path length difference distribution between the first polarization component and the second polarization component that respectively travel from the first polarizing plate and the second polarizing plate to the analyzer, to thereby give a continuous phase change between the first polarization component and the second polarization component;
   e) a spectral optical system for wavelength-resolving the linear interference image, to thereby form an optical spectrum;
   f) a detection unit for detecting a light intensity distribution of the optical spectrum; and
   g) a processing unit for acquiring an amplitude per wavelength and a birefringent phase difference per wavelength of the light emitted from the object to be measured, from the light intensity distribution detected by the detection unit.

4. The optical characteristic measurement device according to claim 1, wherein
   the first polarizing plate and the second polarizing plate are arranged such that polarization directions of the first polarization component and the second polarization component are orthogonal to each other, and are inclined by 45 degrees with respect to an electric field component of the linearly polarized light that enters the object to be measured.

5. The optical characteristic measurement device according to claim 1, wherein
   the division optical system includes an objective lens for collimating the light emitted from the object to be measured into parallel light rays and directing the parallel light rays to the first polarizing plate and the second polarizing plate, and
   the processing unit acquires an amplitude per wavelength and a birefringent phase difference per wavelength of a light emitted from a part of the object to be measured, the part corresponding to a focal point of the objective lens.

6. The optical characteristic measurement device according to claim 5, further comprising a focal point changer for relatively changing the focal point of the objective lens with respect to the object to be measured.

7. An optical characteristic measurement method comprising:
   a) causing a linearly polarized light to enter an object to be measured;
   b) directing, by a division optical system, a light emitted from the object to be measured, on which the linearly polarized light is incident, to a first polarizing plate and a second polarizing plate;
   c) directing a first polarization component transmitted through the first polarizing plate and a second polarization component transmitted through the second polarizing plate to an imaging optical system through an analyzer, while changing a difference in optical path length between the first polarization component and the second polarization component, and focusing, by the imaging optical system, the directed components on a single point, to thereby form an interference image; and
   d) Fourier-transforming data indicating a change in light intensity of the interference image, to thereby acquire an amplitude per wavelength and a birefringent phase difference per wavelength of the light emitted from the object to be measured.

8. An optical characteristic measurement method comprising:
   a) causing a linearly polarized light to enter an object to be measured;
   b) directing, by a division optical system, a light emitted from the object to be measured, on which the linearly polarized light is incident, to a first polarizing plate and a second polarizing plate;
   c) directing a first polarization component transmitted through the first polarizing plate and a second polarization component transmitted through the second polarizing plate to an imaging optical system through an analyzer, while giving a continuous optical path length difference distribution between the first polarization component and the second polarization component, and focusing, by the imaging optical system, the directed components on a single straight line, to thereby form a linear interference image; and
   d) Fourier-transforming data indicating a light intensity distribution of the linear interference image along a direction in which the interference image extends, to thereby acquire an amplitude per wavelength and a birefringent phase difference per wavelength of the light emitted from the object to be measured.

9. An optical characteristic measurement method comprising:
   a) causing a linearly polarized light to enter an object to be measured;
   b) directing, by a division optical system, a light emitted from the object to be measured, on which the linearly polarized light is incident, to a first polarizing plate and a second polarizing plate;
   c) directing a first polarization component transmitted through the first polarizing plate and a second polarization component transmitted through the second polarizing plate to an imaging optical system through an analyzer, while giving a continuous optical path length difference distribution between the first polarization component and the second polarization component, and focusing, by the imaging optical system, the directed components on a single straight line, to thereby form a linear interference image;
   d) wavelength-resolving, by a spectral optical system, the linear interference image, to thereby acquire an optical spectrum; and
   e) acquiring an amplitude per wavelength and a birefringent phase difference per wavelength of the light emitted from the object to be measured, based on a light intensity distribution of the optical spectrum.

10. The optical characteristic measurement device according to claim 2, wherein
   the first polarizing plate and the second polarizing plate are arranged such that polarization directions of the first polarization component and the second polarization component are orthogonal to each other, and are inclined by 45 degrees with respect to an electric field component of the linearly polarized light that enters the object to be measured.

11. The optical characteristic measurement device according to claim 3, wherein
   the first polarizing plate and the second polarizing plate are arranged such that polarization directions of the first polarization component and the second polarization component are orthogonal to each other, and are inclined by 45 degrees with respect to an electric field component of the linearly polarized light that enters the object to be measured.

12. The optical characteristic measurement device according to claim 2, wherein
   the division optical system includes an objective lens for collimating the light emitted from the object to be measured into parallel light rays and directing the parallel light rays to the first polarizing plate and the second polarizing plate, and
   the processing unit acquires an amplitude per wavelength and a birefringent phase difference per wavelength of a light emitted from a part of the object to be measured, the part corresponding to a focal point of the objective lens.

13. The optical characteristic measurement device according to claim 3, wherein
   the division optical system includes an objective lens for collimating the light emitted from the object to be measured into parallel light rays and directing the parallel light rays to the first polarizing plate and the second polarizing plate, and
   the processing unit acquires an amplitude per wavelength and a birefringent phase difference per wavelength of a light emitted from a part of the object to be measured, the part corresponding to a focal point of the objective lens.

14. The optical characteristic measurement device according to claim 12, further comprising a focal point changer for relatively changing the focal point of the objective lens with respect to the object to be measured.

15. The optical characteristic measurement device according to claim 13, further comprising a focal point changer for relatively changing the focal point of the objective lens with respect to the object to be measured.

* * * * *